(12) United States Patent
Low

(10) Patent No.: US 8,293,707 B2
(45) Date of Patent: Oct. 23, 2012

(54) HETERODIMERIC FOLLICLE STIMULATING HORMONE-FC (FSH-FC) FUSION PROTEINS FOR INCREASING FSH ACTIVITY

(75) Inventor: Susan C. Low, Pepperell, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 450 days.

(21) Appl. No.: 12/427,640

(22) Filed: Apr. 21, 2009

(65) Prior Publication Data

US 2010/0291079 A1 Nov. 18, 2010

Related U.S. Application Data

(62) Division of application No. 11/045,022, filed on Jan. 27, 2005, now Pat. No. 7,601,516.

(60) Provisional application No. 60/540,236, filed on Jan. 28, 2004.

(51) Int. Cl.
*A61K 38/24* (2006.01)
(52) U.S. Cl. .................... 514/9.9; 435/69.7; 530/350
(58) Field of Classification Search ................ None
See application file for complete search history.

(56) References Cited

U.S. PATENT DOCUMENTS

| | | | |
|---|---|---|---|
| 4,713,339 A | 12/1987 | Levinson et al. |
| 5,155,027 A | 10/1992 | Sledziewski et al. |
| 5,338,835 A | 8/1994 | Boime |
| 5,428,130 A | 6/1995 | Capon et al. |
| 5,480,981 A | 1/1996 | Goodwin et al. |
| 5,712,121 A | 1/1998 | Devos et al. |
| 5,739,277 A | 4/1998 | Presta et al. |
| 5,767,251 A | 6/1998 | Reddy et al. |
| 5,808,029 A | 9/1998 | Brockhaus et al. |
| 6,030,613 A | 2/2000 | Blumberg et al. |
| 6,086,875 A | 7/2000 | Blumberg et al. |
| 6,193,972 B1 | 2/2001 | Campbell et al. |
| 6,485,726 B1 | 11/2002 | Blumberg et al. |
| 6,653,338 B2 | 11/2003 | El Tayer et al. |
| 7,060,274 B2 | 6/2006 | Blumberg et al. |
| 7,067,129 B2 | 6/2006 | Blumberg et al. |
| 7,601,516 B2 | 10/2009 | Low |
| 2003/0211580 A1 | 11/2003 | Lustbader |
| 2003/0235536 A1 | 12/2003 | Blumberg et al. |
| 2004/0063912 A1 | 4/2004 | Blumberg et al. |

FOREIGN PATENT DOCUMENTS

| | | |
|---|---|---|
| WO | WO 96/32478 A1 | 10/1996 |
| WO | WO 97/34631 A1 | 9/1997 |
| WO | WO 03/077834 A2 | 9/2003 |
| WO | WO 2004/004798 A2 | 1/2004 |
| WO | WO 2005/073383 A2 | 8/2005 |

OTHER PUBLICATIONS

Foresta et al., Fertility and Sterility, 2002; 77: 238-244.*
Website downloaded May 6, 2011 from the Mayo Clinic: mayoclinic.com/health/infertility/DS00310/METHOD=print&DSECTION=all; 20 pages total.*
Website downloaded Apr. 28, 2011 from partsregistry.org/wiki/index.php?title=Part:BBa_K243006; 1 page total.*
Arai et al., Protein Engineering, 2001; 14: 529-432.*
Low et al., Human Reproduction, 2005; 20: 1805-1813.*
George and Heringa, Protein Engineering, 2003; 15: 871-879.*
Armour, K.L., et al., "Recombinant human IgG molecules lacking Fcγ receptor I binding and monocyte triggering activities," *Eur. J. Immunol.* 29(8): 2613-24, Wiley-VCH, Germany (Aug. 1999).
Bitonti, A.J., et al., "Pulmonary delivery of an erythropoietin Fc fusion protein in non-human primates through an immunoglobulin transport pathway," *Proc. Natl. Acad. Sci. U.S.A.* 101(26): 9763-8, National Academy of Sciences, United States (Jun. 2004).
Bouloux, P.M., et al., "First human exposure to FSH-CTP in hypogonadotrophic hypogonadal males," *Hum. Reprod.* 16(8): 1592-7, Oxford University Press, England (Aug. 2001).
Burmeister, W.P., et al., "Crystal structure of the complex of rat neonatal Fc receptor with Fc.," *Nature* 372(6504): 379-83, Nature Publishing Group, England (Nov. 1994).
Capon, D.J., et al., "Designing CD4 immunoadhesins for AIDS therapy," *Nature* 337(6207): 525-31, Nature Publishing Group, England (Feb. 1989).
Dahl, K.D., et al., "Monitoring the menstrual cycle of humans and lowland gorillas based on urinary profiles of bioactive follicle-stimulating hormone and steriod metabolites," *J. Clin. Endocrinol Metab.* 64(3): 486-93, Endocrine Society, United States (Mar. 1987).
Daya, S., "Follicle-stimulating hormone in clinical practice: an update." *Treat. Endocrinol.* 3(3): 161-71, Adis International, New Zealand (2004).
Dorrington, J.H. & Armstrong, D.T., "Follicle-stimulating hormone stimulates estradiol-17β synthesis in cultured Sertoli cells," *Proc. Natl. Acad. Sci. U.S.A.* 72(7): 2677-81, National Academy of Sciences, United States (Jul. 1975).
Duijkers, I.J., et al., "Single dose pharmacokinetics and effects on follicular growth and serum hormones of a long-acting recombinant FSH preparation (FSH-CTP) in healthy pituitary-suppressed females," *Hum. Reprod.* 17(8): 1987-93, Oxford University Press, England (Aug. 2002).
Friend, P.J., et al., "Phase I study of an engineered aglycosylated humanized CD3 antibody in renal transplant rejection," *Transplantation* 68(11): 1632-7, Lippincott Williams & Wilkins, United States (Dec. 1999).
Ip, A.Y., et al., "Stability of recombinant consensus interferon to air-jet and ultrasonic nebulization," *J. Pharm. Sci.* 84(10): 1210-4, Wiley, United States (Oct. 1995).

(Continued)

*Primary Examiner* — Bridget E Bunner
*Assistant Examiner* — Christina Borgeest
(74) *Attorney, Agent, or Firm* — Sterne, Kessler, Goldstein & Fox PLLC

(57) ABSTRACT

The invention provides novel heterodimeric fusion proteins comprising a first polypeptide including an alpha subunit of FSH (αFSH) linked directly or indirectly to a binding partner of neonatal Fc receptor (FcRn) and a second polypeptide including a beta subunit of FSH (βFSH) linked directly or indirectly to an FcRn binding partner. In one embodiment the FcRn binding partner includes an Fc fragment of an immunoglobulin, e.g., an Fc fragment of IgG. Also provided are methods making and using the fusion proteins of the invention. The invention provides a method for increasing fertility in a subject and a method for treating a subject having a disease state responsive to treatment by FSH.

19 Claims, 13 Drawing Sheets

OTHER PUBLICATIONS

Israel, E.J., et al., "Expression of the neonatal Fc receptor, FcRn, on human intestinal epithelial cells," *Immunology* 92(1): 69-74, Blackwell Scientific Publications, England (Sep. 1997).

Jia, X.C. & Hsueh, A.J., "Granulosa cell aromatase bioassay for follicle-stimulating hormone: validation and application of the method," *Endocrinology* 119(4): 1570-7, Endocrine Society, United States (Oct. 1986).

Kainoh, M. & Tanaka, T., "Production of soluble integrin α2β1 heterodimer complex functionally active in vitro and in vivo," *Biochem. Biophys. Res. Commun.* 290(1): 305-10, Academic Press, United States (Jan. 2002).

Keene, J.L., et al., "Expression of biologically active human follitropin in Chinese hamster ovary cells," *J. Biol. Chem.* 264(9): 4769-75, American Society for Biochemistry and Molecular Biology, United States (Mar. 1989).

Klein, J., et al., "Development and characterization of a long-acting recombinant hFSH agonist," *Hum. Reprod.* 18(1): 50-6, Oxford University Press, England (Jan. 2003).

Klein, J., et al., "Pharmacokinetics and pharmacodynamics of single-chain recombinant human follicle-stimulating hormone containing the human chorionic gonadotropin carboxyterminal peptide in the rhesus monkey," *Fertil. Steril.* 77(6): 1248-55, Elsevier for the American Society for Reproductive Medicine, United States (Jun. 2002).

Kobayashi, N., et al., "FcRn-mediated transcytosis of immunoglobulin G in human renal proximal tubular epithelial cells," *Am. J. Physiol. Renal. Physiol.* 282(2): F358-65, American Physiological Society, United States (Feb. 2002).

Layman, L.C., et al., "FSHβ gene mutations in a female with partial breast development and a male sibling with normal puberty and azoospermia," *J. Clin. Endocrinol Metab.* 87(8): 3702-7, Endocrine Society, United States (Aug. 2002).

Ie Cotonnec, J.Y., et al., "Clinical pharmacology of recombinant human follicle-stimulating hormone. II. Single doses and steady state pharmacokinetics," *Fertil. Steril.* 61(4): 679-86, Elsevier for the American Society of Reproductive Medicine, United States (Apr. 1994).

Meachem, S.J., "Neonatal exposure of rats to recombinant follicle stimulating hormone increases adult Sertoli and spermatogenic cell numbers," *Biol Reprod.* 54(1): 36-44, Society for the Study of Reproduction, United States (Jan. 1996).

Niven, R.W., "Delivery of biotherapeutics by inhalation aerosol," *Crit. Rev. Ther. Drug. Carrier Syst.* 121(2-3): 151-231, Begell House, United States (1995).

Padmanabhan, V., et al., "An improved in vitro bioassay for follicle-stimulating hormone (FSH): suitable for measurement of FSH in unextracted human serum," *Endocrinology* 121(3): 1089-98, Endocrine Society, United States (Sep. 1987).

Prochet, H.C., et al., "Clinical pharmacology of recombinant human follicle-stimulating hormone. III. Pharmacokinetic-pharmacodynamic modeling after repeated subcutaneous administration," *Fertil. Steril.* 61(4): 687-95, Elsevier for the American Society for Reproductive Medicine, United States (Apr. 1994).

Prochet, H.C., et al., "Pharmacokinetics of recombinant human follicle stimulating hormone after intravenous, intramuscular, and subcutaneous administration in monkeys, and comparison with intravenous administration of urinary follicle stimulating hormone," *Drug Metab. Dispos.* 21(1): 144-50, American Society for Pharmacology and Experimental Therapeutics, United States (Jan.-Feb. 1993).

Powell, M.F., et al., "Compendium of excipients for parenteral formulations," *PDA J. Pharm. Sci. Technol.* 52(85): 238-311, Pda (Parenteral Drug Association), United States (Sep.-Oct. 1998).

Shields, R.L., et al., "High resolution mapping of the binding site on human IgG1 for FcγRI, FcγRII, FcγRIII and FcRn and design of the IgG1 variants with improved binding to the FcγR," *J. Biol. Chem.* 276(9): 6591-604, American Society for Biochemistry and Molecular Biology, United States (Marh 2001; Epub Nov. 2000).

Spiekermann, G.M., et al., "Receptor-mediated immunoglobulin G transport across mucosal barriers in adult life: functional expression of FcRn in the mammalian lung," *J. Exp. Med.* 196(3): 303-10, Rockefeller University Press, United States (Aug. 2002).

Story, C.M., et al., "A major histocompatibility complex class I-like Fc receptor cloned from human placenta: possible role in transfer of immunoglobulin G from mother to fetus," *J. Exp. Med.* 180(6): 2377-81, Rockefeller University Press, United States (Dec. 1994).

Sugahara, T., et al., "Expression of biologically active fusion genes encoding the common α subunit and the follicle-stimulating hormone β subunit. Role of a linker sequence," *J. Biol. Chem.* 271(18): 10445-8, American Society for Biochemistry and Molecular Biology, United States (May 1996).

Tano, M., et al., "Application of Chinese hamster ovary cells transfected with the recombinant human follicle-stimulating hormone (FSH) receptor for measurement for serum FSH," *Fertil. Steril.* 64(6): 1120-4, Elsevier for the American Society for Reproductive Medicine, United States (Dec. 1995).

Themmen, A.P.N. & Huhtaniemi, I.T., "Mutations of gonadotropins and gonadotropin receptors: elucidating the physiology and pathophysiology of pituitary-gonadal function," *Endocr. Rev.* 21(5): 551-83, Endocrine Society, United States (Oct. 2000).

Ward, E.S. & Ghetie, V., "The effector functions of immunoglobulins: implications for therapy," *Ther. Immunol.* 2(2): 77-94, Blackwell Scientific Publications, England (Apr. 1995).

Weinbauer, G.F., et al., "Pharmacokinetics and pharmacodynamics of recombinant and urinary human FSH in the male monkey (*Macaca fascicularis*)," *J. Endocrinol.* 141(1): 113-21, Society for Endocrinology, England (Apr. 1994).

International Search Report for International Application No. PCT/US2005/003034, European Patent Office, Rijswijk, Netherlands, mailed on Jul. 9, 2005.

Office Communication mailed Jan. 9, 2007, in European Patent Application No. 05 712 467.9, Syntonix Pharmaceuticals, Inc., filed Jan. 27, 2005.

Office Communication mailed Jan. 29, 2008, in European Patent Application No. 05 712 467.9, Syntonix Pharmaceuticals, Inc., filed Jan. 27, 2005.

Office Communication mailed Aug. 4, 2010, in European Patent Application No. 05 712 467.9, Syntonix Pharmaceuticals, Inc., filed Jan. 27, 2005.

\* cited by examiner

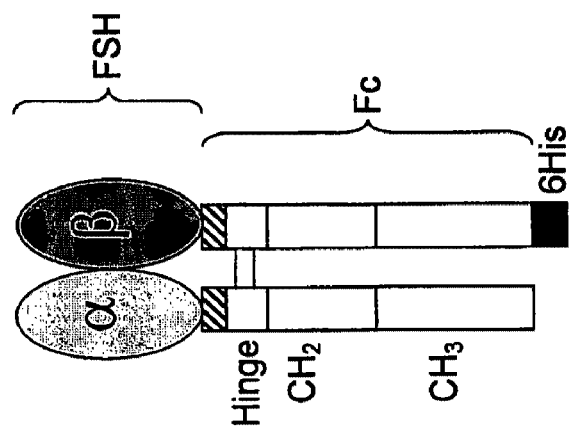
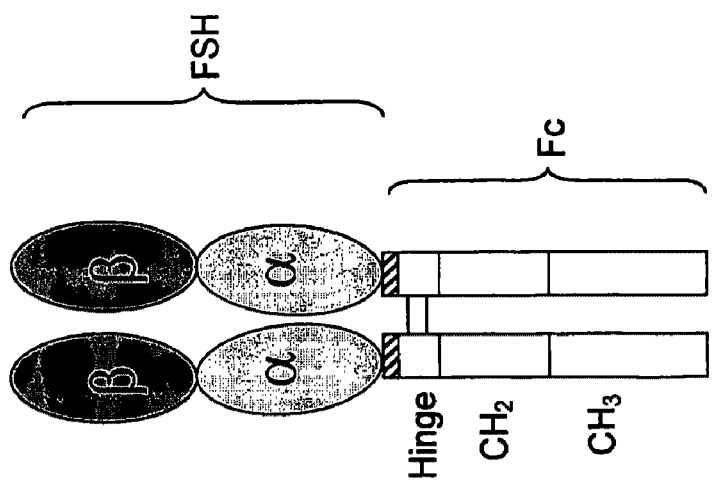
Figure 1c

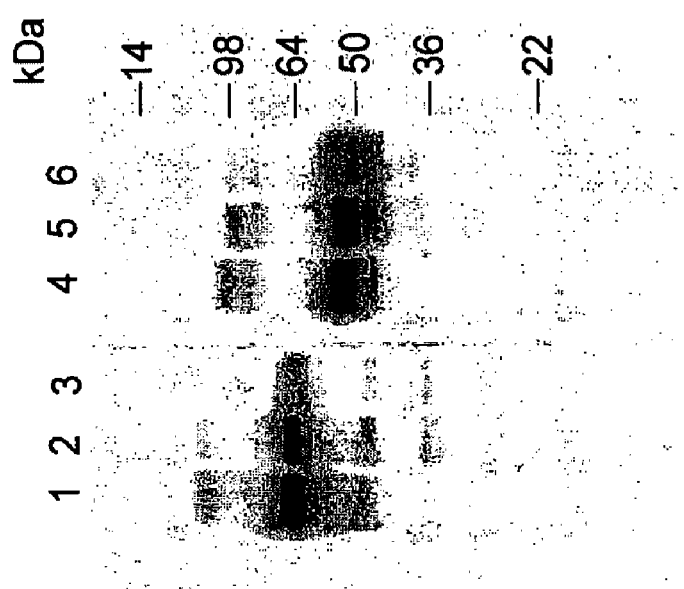

Single Chain FSH-Fc

SEQUENCE LISTING

```
<160> NUMBER OF SEQ ID NOS: 18

<210> SEQ ID NO 1
<211> LENGTH: 1090
<212> TYPE: DNA
<213> ORGANISM: Homo sapiens

<400> SEQUENCE: 1
cctgcaggcc accatggatt actacagaaa atatgcagct atctttctgg tcacattgtc      60
ggtgtttctg catgttctcc attccgctcc tgatgtgcag gattgcccag aatgcacgct     120
acaggaaaac ccattcttct cccagccggg tgccccaata cttcagtgca tgggctgctg     180
cttctctaga gcatatccca ctccactaag gtccaagaag acgatgttgg tccaaaagaa     240
cgtcacctca gagtccactt gctgtgtagc taaatcatat aacagggtca cagtaatggg     300
gggtttcaaa gtggagaacc acacggcgtg ccactgcagt acttgttatt atcacaaatc     360
tggtggaggc ggatccggtg gaggcgggtc cggcggtgga gggagcgaca aaactcacac     420
gtgcccgccg tgcccagctc cggaactgct gggcggaccg tcagtcttcc tcttcccccc     480
```

-continued

```
aaaacccaag gacaccctca tgatctcccg gacccctgag gtcacatgcg tggtggtgga     540
cgtgagccac gaagaccctg aggtcaagtt caactggtac gtggacggcg tggaggtgca     600
taatgccaag acaaagccgc gggaggagca gtacaacagc acgtaccgtg tggtcagcgt     660
cctcaccgtc ctgcaccagg actggctgaa tggcaaggag tacaagtgca aggtctccaa     720
caaagccctc ccagccccca tcgagaaaac catctccaaa gccaagggc agccccgaga     780 accacaggtg tacaccctgc ccccatcccg ggatgagctg accaagaacc aggtcagcct     840
gacctgcctg gtcaaaggct tctatcccag cgacatcgcc gtggagtggg agagcaatgg     900
gcagccggag aacaactaca agaccacgcc tcccgtgttg gactccgacg gctccttctt     960
cctctacagc aagctcaccg tggacaagag caggtggcag caggggaacg tcttctcatg    1020
ctccgtgatg catgaggctc tgcacaacca ctacacgcag aagagcctct ccctgtctcc    1080
gggtaaatga                                                           1090
```

<210> SEQ ID NO 2
<211> LENGTH: 358
<212> TYPE: PRT
<213> ORGANISM: Homo sapiens

<400> SEQUENCE: 2

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser Gly Gly Gly Ser Gly Gly Gly Ser Gly Gly
        115                 120                 125

Gly Gly Ser Asp Lys Thr His Thr Cys Pro Pro Cys Pro Ala Pro Glu
130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270
```

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
        290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 3
<211> LENGTH: 1147
<212> TYPE: DNA
<213> ORGANISM: Homo sapiens

<400> SEQUENCE: 3
cctgcaggcc accatgaaga cactccagtt tttcttcctt ttctgttgct ggaaagcaat      60
ctgctgcaat agctgtgagc tgaccaacat caccattgca atagagaaag aagaatgtcg     120
tttctgcata agcatcaaca ccacttggtg tgctggctac tgctcaccca gggatctggt     180
gtataaggac ccagccaggc ccaaaatcca gaaaacatgt accttcaagg aactggtata     240
cgaaacagtg agagtgcccg ctgtgctca ccatgcagat tccttgtata catacccagt     300
ggccacccag tgtcactgtg gcaagtgtga cagcgacagc actgattgta ctgtgcgagg     360
cctggggccc agctactgct cctttggtga atgaaagaa ggtggaggcg atccggtgg      420
aggcgggtcc ggcggtggag ggagcgacaa aactcacacg tgcccgccgt gcccagctcc     480
ggaactgctg ggcggaccgt cagtcttcct cttcccccca aaacccaagg acaccctcat     540
gatctcccgg acccctgagg tcacatgcgt ggtggtggac gtgagccacg aagaccctga     600
ggtcaagttc aactggtacg tggacggcgt ggaggtgcat aatgccaaga caaagccgcg     660
ggaggagcag tacaacagca cgtaccgtgt ggtcagcgtc ctcaccgtcc tgcaccagga     720
ctggctgaat ggcaaggagt acaagtgcaa ggtctccaac aaagcctcc cagccccat      780
cgagaaaacc atctccaaag ccaaagggca gccccgagaa ccacaggtgt acaccctgcc     840
cccatcccgg gatgagctga ccaagaacca ggtcagcctg acctgcctgg tcaaaggctt     900
ctatcccagc gacatcgccg tggagtggga gagcaatggg cagccggaga caactacaa      960
gaccacgcct cccgtgttgg actccgacgg ctccttcttc ctctacagca agctcaccgt    1020
ggacaagagc aggtggcagc aggggaacgt cttctcatgc tccgtgatgc atgaggctct    1080
gcacaaccac tacacgcaga gagcctctc cctgtctccg ggtaaacatc atcaccatca    1140
ccactga                                                            1147

<210> SEQ ID NO 4
<211> LENGTH: 377
<212> TYPE: PRT
<213> ORGANISM: Homo sapiens

<400> SEQUENCE: 4

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
 50                  55                  60

Ile Gln Lys Thr Cys Thr Phe Lys Glu Leu Val Tyr Glu Thr Val Arg
 65                  70                  75                  80

Val Pro Gly Cys Ala His His Ala Asp Ser Leu Tyr Thr Tyr Pro Val
                 85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Gly Gly Gly Ser Gly Gly Gly Gly Ser Gly Gly Gly Gly Ser
        130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Asp Glu Leu Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys His His His His His
    370                 375

<210> SEQ ID NO 5
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 5
ggctagcctg caggccacca tggattacta cagaaaatat gc        42

```
<210> SEQ ID NO 6
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 6
tccaccggat ccgcctccac cagatttgtg ataataacaa gtact           45

<210> SEQ ID NO 7
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 7
ggctagcctg caggccacca tgaagacact ccagtttttc t               41

<210> SEQ ID NO 8
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 8
tccaccggat ccgcctccac cttctttcat ttcaccaaag ga              42

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Glu Phe Ala Gly Ala Ala Ala Val
1               5

<210> SEQ ID NO 10
<211> LENGTH: 15
<212> TYPE: PRT
<213> ORGANISM: Artificial sequence
<220> FEATURE:
<223> OTHER INFORMATION: Synthetic peptide

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Pro Lys Asn Ser Ser Met Ile Ser Asn Thr Pro
1               5                   10

<210> SEQ ID NO 12
<211> LENGTH: 7
<212> TYPE: PRT
<213> ORGANISM: Artificial sequence
<220> FEATURE:
```

<223> OTHER INFORMATION: Synthetic peptide

<400> SEQUENCE: 12

His Gln Ser Leu Gly Thr Gln
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic peptide

<400> SEQUENCE: 13

His Gln Asn Leu Ser Asp Gly Lys
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

His Gln Asn Ile Ser Asp Gly Lys
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Val Ile Ser Ser His Leu Gly Gln
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Ser Gly Gly Ser Gly Gly Ser
1               5

<210> SEQ ID NO 17
<211> LENGTH: 15
<212> TYPE: PRT
<213> ORGANISM: Artificial sequence
<220> FEATURE:
<223> OTHER INFORMATION: Synthetic peptide

<400> SEQUENCE: 17

Gly Gly Ser Gly Gly Ser Gly Gly Ser Gly Gly Ser Gly Gly Gly
1               5                   10                  15

<210> SEQ ID NO 18
<211> LENGTH: 18
<212> TYPE: PRT
<213> ORGANISM: Artificial sequence
<220> FEATURE:
<223> OTHER INFORMATION: Synthetic peptide

```
<400> SEQUENCE: 18

Gly Gly Ser Gly Gly Ser Gly Gly Ser Gly Gly Ser Gly Gly Ser Gly
1               5                   10                  15

Gly Ser
```

HETERODIMERIC FOLLICLE STIMULATING HORMONE-FC (FSH-FC) FUSION PROTEINS FOR INCREASING FSH ACTIVITY

CROSS-REFERENCE TO RELATED APPLICATIONS

This application is a divisional application of U.S. application Ser. No. 11/045,022, filed Jan. 27, 2005 and issued Oct. 13, 2009 as U.S. Pat. No. 7,601,516, which claims benefit under 35 U.S.C. 119(e) of U.S. Provisional Patent Application Ser. No. 60/540,236, filed on Jan. 28, 2004, the entire content of which is incorporated herein by reference.

FIELD OF THE INVENTION

The invention relates generally to the field of therapeutics for reproductive disorders. More specifically, the invention relates to heterodimeric follicle stimulating hormone-Fc fusion proteins for the treatment of infertility.

BACKGROUND OF THE INVENTION

Infertility affects one in ten couples, resulting in millions of couples struggling to become pregnant. Many of these couples are potential candidates for infertility treatment. Follicle stimulating hormone (FSH), either extracted from urine or produced recombinantly, is a parenterally-administered protein product used by specialists to increase fertility and has been so used clinically since the 1960's. For example, FSH is used for ovulation induction (OI) and for controlled ovarian hyperstimulation (COH). Whereas OI is directed at achieving a single follicle to ovulate, COH is directed at harvesting multiple oocytes for use in various in vitro assisted reproductive technologies (e.g., for in vitro fertilization). FSH is also used in gonadotropin replacement therapy in males.

The use of FSH is limited by its high cost, the need for extensive monitoring by specialist physicians, by lack of oral dosing or other noninvasive routes of administration, and the need for daily patient injections. Recombinant FSH suffers from a short half-life and correspondingly diminished biopotency, necessitating frequent administration and limited clinical usefulness. For example, recombinant human FSH (hFSH) must be administered as a daily intramuscular or subcutaneous injection, often for 8 to 12 days or more when used for ovulation induction. These regimens are associated with a number of side effects, including local irritation and discomfort, which result in poor compliance and a reduction in therapeutic efficacy. Thus, there exists a need for forms of FSH with increased half-life and bioavailability as compared to traditional forms of FSH therapy.

Follicle stimulating hormone (FSH) is found in nature as a non-covalently linked heterodimeric protein consisting of an alpha ($\alpha$) subunit and a beta ($\beta$) subunit (Pierce J G and Parsons T F (1981) *Ann Rev Biochem* 50:465-95). Subunit assembly has been reported to be essential for bioactivity of FSH (Jia X C and Hseuh A J W (1986) *Endocrinology* 119: 1570-7) as well as for the stability of the beta subunit (Keene et al. (1989) *J Biol Chem* 264:4769-75).

One approach to improve FSH therapy has been by increasing the glycosylation of the protein. Other approaches have included carboxy terminal portion (CTP) extended forms of FSH (see e.g., U.S. Pat. No. 5,338,835, and U.S. 2003/0211580 A1) or FSH mimetics (see e.g., U.S. Pat. No. 6,653,338) for the treatment of infertility. Early attempts, however, to improve half-life and bioactivity have yet to result in a therapeutically effective drug capable of providing advantages over existing therapies.

It has also been reported that a single-chain fusion of the $\alpha$ and $\beta$ subunits of FSH (single-chain FSH) is fully active (Sugahara et al. (1996) *J Biol Chem* 271:10445-8). Single-chain FSH is reported to have an increased serum half-life when fused with the carboxyterminal peptide of human chorionic gonadotropin (hCG). (See Klein et al. (2003) *Hum Reprod* 18:50-6; Bouloux et al. (2001) *Hum Reprod* 16:1592-7; Duijkers et al. (2002) *Hum Reprod* 17:1987-93.)

The use of heterodimeric FSH and its formulation are fraught with stability and purification issues not present with single-chain FSH. While recombinant FSH is known (see e.g., U.S. Pat. No. 5,767,251), keeping the alpha and beta subunits associated in a way that results in a biologically active molecule useful for therapeutic purposes, and in particular with long-acting forms of heterodimeric FSH, remained a challenge until the present invention.

The creation of fusion proteins comprised of immunoglobulin constant regions linked to a protein of interest, or fragment thereof, has been described (see, e.g., U.S. Pat. Nos. 5,155,027, 5,428,130, 5,480,981, and 5,808,029). These molecules usually possess both the biological activity associated with the linked molecule of interest as well as the effector function, or some other desired characteristic, associated with the immunoglobulin constant region. Fusion proteins comprising an Fc portion of an immunoglobulin can bestow several desirable properties on a fusion protein including increased stability, increased serum half-life (see Capon et al. (1989) *Nature* 337:525) as well as binding to Fc receptors such as the neonatal Fc receptor (FcRn) (U.S. Pat. Nos. 6,086,875, 6,030,613, and 6,485,726).

FcRn is active in adult epithelial tissue and expressed in the lumen of the intestines, pulmonary airways, nasal surfaces, vaginal surfaces, colon and rectal surfaces (U.S. Pat. No. 6,485,726). Fusion proteins comprised of FcRn binding partners (e.g., IgG, Fc fragments) can be effectively shuttled across epithelial barriers by FcRn, thus providing a non-invasive means to systemically administer a desired therapeutic molecule. Additionally, fusion proteins comprising an FcRn binding partner are endocytosed and protected by cells expressing the FcRn. Instead of being marked for degradation, these fusion proteins are recycled out into circulation again, thus increasing the in vivo half-life of these proteins.

FSH has been conjugated to Fc as described in U.S. 2003/0235536 A1. However, therein is described single-chain FSH-Fc fusion protein for delivery to the central airways of non-human primates. Single-chain FSH-Fc fusions contain hFSH$\beta\alpha$-Fc, in a single-chain with the beta and alpha subunits conjugated end-to-end and the two polypeptide chains of the fusion are identical (see FIG. 1c). As shown in FIG. 1c, single-chain FSH-Fc forms a homodimer.

SUMMARY OF THE INVENTION

The invention relates to fusion proteins of heterodimeric FSH wherein the alpha and beta subunits of FSH are each conjugated to an FcRn binding partner or to an Fc fragment. In one embodiment, the invention provides fusion proteins having two polypeptide chains, one chain having at least $\alpha$FSH, linked directly or indirectly through an optional linker to an Fc fragment of an immunoglobulin, and the second chain having $\beta$FSH, also linked directly or indirectly through an optional linker to an Fc fragment of an immunoglobulin. By way of these fusion proteins, the invention provides methods for increasing the half-life of FSH and, therefore, further provides an effective means for increasing a subject's fertility with reduced dosing frequency and/or treating a disease state responsive to FSH therapy.

In contrast to the single-chain FSH-Fc fusion protein described in U.S. 2003/0235536 A1, the heterodimeric FSH-Fc fusion proteins of the present invention (FIG. 1c) have the alpha subunit of FSH conjugated to one Fc chain and the beta subunit of FSH conjugated to the other Fc chain, wherein the alpha and beta subunits are aligned head-to-head and tail-to-tail and the Fc fragments are similarly aligned head-to-head and tail-to-tail. The two chains are brought into association with one another by the interactions between the alpha and beta subunits of FSH as exist, for example, with endogenous FSH. Alternatively, or in addition thereto, the association of the two Fc chains, as for example through a disulfide bond(s), brings the alpha and beta subunits of FSH in proximity to each other thus enhancing its bioactivity as compared to single-chain FSH fusion proteins.

In one aspect the invention is a heterodimeric fusion protein including two associated polypeptide chains, the first chain including an alpha subunit of follicle stimulating hormone (αFSH) conjugated to a neonatal Fc receptor (FcRn) binding partner and the second chain including a beta subunit of FSH (βFSH) conjugated to an FcRn binding partner, wherein the head of αFSH is aligned with the head of βFSH and the tails of each of the respective FcRn binding partners are aligned.

In one aspect the invention is a fusion protein including two polypeptide chains of the formula

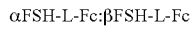

αFSH-L-Fc:βFSH-L-Fc wherein αFSH is an alpha subunit of FSH, βFSH is a beta subunit of FSH, L is a linker or direct bond, and Fc is an Fc fragment of an immunoglobulin, wherein carboxy termini of αFSH and βFSH are linked either directly or indirectly through L to the amino terminus of the respective Fc, further wherein the colon (:) represents an association between the two polypeptide chains of the fusion protein, and further wherein the head of αFSH is aligned with the head of βFSH and the tails of each of the respective Fc fragments are aligned.

In one aspect the invention is a fusion protein including two polypeptide chains of the formula

Fc-L-αFSH:Fc-L-βFSH wherein αFSH is the alpha subunit of FSH, βFSH is the beta subunit of FSH, L is a linker or direct bond, and Fc is an Fc fragment of an immunoglobulin, wherein the amino termini of αFSH and βFSH are linked either directly or indirectly through L to the carboxy terminus of the respective Fc, further wherein the colon (:) represents an association between the two polypeptide chains of the fusion protein, and further wherein the head of αFSH is aligned with the head of βFSH and the tails of each of the respective Fc fragments are aligned.

In one embodiment the fusion protein of the invention can include at least one tag moiety. The tag moiety can be used, for example, to assist in purification or identification of recombinantly produced polypeptide or protein. For example, in one embodiment one polypeptide of the heterodimeric fusion protein further includes a histidine tag.

The invention in one aspect is a pharmaceutical composition which includes a fusion protein of the invention and a pharmaceutically acceptable excipient.

In another aspect the invention is a method for increasing a subject's fertility. The method according to this aspect of the invention includes the step of administering to the subject an amount of a fusion protein of the invention effective to enhance fertility of the subject.

In one aspect the invention is a method for treating a subject having a disease state responsive to treatment by FSH. The method according to this aspect of the invention includes the step of administering to the subject an effective amount of a fusion protein of the invention.

In one aspect the invention is a method of increasing the half-life of heterodimeric FSH. The method according to this aspect of the invention includes the step of conjugating, directly or indirectly through a linker, each of an alpha subunit and a beta subunit of FSH to an FcRn binding partner, wherein the head of the αFSH is aligned with the head of βFSH and the tails of each of the respective FcRn binding partners are aligned.

BRIEF DESCRIPTION OF THE DRAWINGS

FIG. 5 is an image of an SDS-PAGE gel showing the effects of excess IgG on the oral uptake of single-chain FSH-Fc and heterodimer FSH-Fc in neonatal rats. Lane 1, 50,000 cpm input single-chain FSH-Fc; Lane 2, $^{125}$I-single-chain FSH-Fc; Lane 3, $^{125}$I-single-chain FSH-Fc in the presence of excess IgG; Lane 4, 50,000 cpm input heterodimer FSH-Fc; Lane 5, $^{125}$I-heterodimer FSH-Fc; Lane 6, $^{125}$I-heterodimer FSH-Fc in the presence of excess IgG.

DETAILED DESCRIPTION

Definitions

Figure 1A:
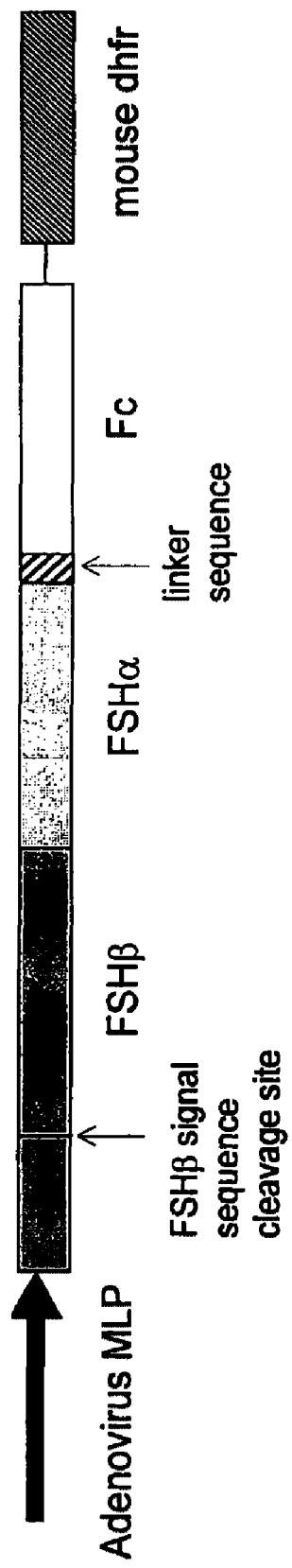
FIG. 1 is a series of schematic diagrams depicting (a) DNA construct made to create single-chain FSH-Fc protein, (b) DNA constructs made to create heterodimer FSH-Fc protein, and (c) single-chain FSH-Fc and heterodimer FSH-Fc proteins.

Affinity tag, as used herein, means a molecule attached to a second molecule of interest, capable of interacting with a specific binding partner for the purpose of isolating or identifying said second molecule of interest.

Analogs of, or proteins or peptides or substantially identical to the fusion proteins of the invention, as used herein, means that a relevant amino acid sequence of a protein or a peptide is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences is determined by standard alignment algorithms such as, for example, Basic Local Alignment Tool (BLAST) described in Altschul et al. (1990) *J. Mol. Biol.*, 215:403-410; the algorithm of Needleman et al. (1970) *J. Mol. Biol.*, 48:444-453; the algorithm of Meyers et al. (1988) *Comput. Appl. Biosci.*, 4:11-17; or Tatusova et al. (1999) *FEMS Microbiol. Lett.*, 174:247-250, etc. Such algorithms are incorporated into the BLASTN, BLASTP and "BLAST 2 Sequences" programs. When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

Bioavailability, as used herein, means the extent and/or rate at which a substance is absorbed into a living system or is made available at the site of physiological activity.

DNA construct, as used herein, means a DNA molecule, or a clone of such a molecule, either single- or double-stranded, that has been modified through human intervention to contain segments of DNA combined in a manner that as a whole would not otherwise exist in nature. DNA constructs contain the information necessary to direct the expression of polypeptides of interest. DNA constructs can include promoters, enhancers and transcription terminators. DNA constructs containing the information necessary to direct the secretion of a polypeptide will typically also contain at least one secretory signal sequence.

A fragment, as used herein with respect to a peptide, polypeptide, or protein, refers to a peptide or polypeptide comprising an amino acid sequence of at least 2 contiguous amino acid residues, of at least 5 contiguous amino acid residues, of at least 10 contiguous amino acid residues, of at least 15 contiguous amino acid residues, of at least 20 contiguous amino acid residues, of at least 25 contiguous amino acid residues, of at least 40 contiguous amino acid residues, of at least 50 contiguous amino acid residues, of at least 100 contiguous amino acid residues, or of at least 200 contiguous amino acid residues or any deletion or truncation of a protein.

FSH and, equivalently except where otherwise noted, heterodimeric FSH, refer to a heterodimeric follicle stimulating hormone glycoprotein composed of an alpha subunit (αFSH; FSH alpha) and a beta subunit (βFSH; FSH beta). FSH and heterodimeric FSH shall refer to naturally occurring forms of FSH and recombinant analogs thereof. In humans the alpha and beta subunits are encoded in separate genes on separate chromosomes. FSH and heterodimeric FSH are to be distinguished from single-chain FSH and single-chain FSH fusion proteins, as well as from the heterodimeric FSH fusion proteins of the instant invention.

A fusion protein, as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A fusion protein can include for example, a protein derived from at least two different biological sources. A biological source can include any non-synthetically produced nucleic acid or amino acid sequence (e.g., a genomic or cDNA sequence, an RNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A fusion protein can also include a protein derived from at least 2 different synthetic sources or a protein derived from at least one biological source and at least one synthetic source.

Linked, as used herein with respect to nucleic acid sequences, refers to a first nucleic acid sequence covalently joined to a second nucleic acid sequence. The first nucleic acid sequence can be directly joined or juxtaposed to the second nucleic acid sequence or alternatively an intervening sequence or linker moiety can covalently join the first sequence to the second sequence. Linked, as used herein with respect to amino acid sequences, refers to a first amino acid sequence covalently joined to a second amino acid sequence. The first amino acid sequence can be directly joined or juxtaposed to the second amino acid sequence or alternatively an intervening sequence or linker moiety can covalently join the first amino acid sequence to the second amino acid sequence. Linked can also refer to a first amino acid sequence non-covalently joined to a second amino acid sequence.

Moderate stringency, as used herein with respect to nucleic acid hybridization, includes conditions that can be readily determined by those having ordinary skill in the art based on, for example, the length of the DNA. The basic conditions are set forth by Sambrook et al. *Molecular Cloning: A Laboratory Manual*, 2 ed. Vol. 1, pp. 1.101-104, Cold Spring Harbor Laboratory Press (1989), and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

High stringency, as used herein with respect to nucleic acid hybridization, includes conditions readily determined by the skilled artisan based on, for example, the length of the DNA. Generally, such conditions are defined as hybridization conditions as above, and with washing at approximately 68° C., 0.2×SSC, 0.1% SDS. The skilled artisan will recognize that the temperature and wash solution salt concentration can be adjusted as necessary according to factors such as the length of the probe.

Polypeptide, as used herein, refers to a polymer of amino acids and does not refer to a specific length of the product; thus, peptides, oligopeptides, and proteins are included within the definition of polypeptide. This term does not exclude post-expression modifications of the polypeptide, for example, glycosylation, acetylation, phosphorylation, pegylation, addition of a lipid moiety, or the addition of any organic or inorganic molecule. Included within the definition are, for example, polypeptides containing one or more analogs of an amino acid (including, for example, unnatural amino acids) and polypeptides with substituted linkages, as well as other modifications known in the art, both naturally occurring and non-naturally occurring.

Serum (or plasma) half-life, abbreviated "$t_{1/2}$", as used herein means elimination half-life, i.e., the time taken for the serum (or plasma) concentration of an agent to fall by one half. The related term "increased serum half-life" is used herein to reference a heterodimeric FSH-Fc fusion protein that is cleared at a slower rate than native FSH alone (whether endogenous, recombinant or synthetic forms thereof).

Treat, treatment, and treating, as used herein, mean any of the following: reduction in severity of any disorder or disease state responsive to treatment by therapy; the prophylaxis of one or more symptoms associated with such disorders or disease states; the reduction in the duration of a disease course of such abnormalities; the provision of beneficial effects to a subject having such abnormalities, without necessarily curing an abnormality or disorder. As used herein with respect to FSH, treat, treatment, and treating mean any of the following: reduction in severity of any reproductive disorder or disease state responsive to treatment by FSH therapy; the prophylaxis of one or more symptoms associated with such disorders or disease states; the reduction in the duration of a disease course of FSH abnormalities; the provision of beneficial effects to a subject having such abnormalities (e.g., increasing fertility), without necessarily curing an FSH abnormality or reproductive disorder.

A. Improved Therapeutics for Infertility

The invention relates generally to improved therapeutics for reproductive disorders or disease states associated with the reproductive system, and in particular, FSH abnormalities. The invention thus relates to a fusion protein of heterodimeric FSH wherein the alpha and beta subunits of FSH are each respectively conjugated to an Fc fragment or to an FcRn binding partner. The fusion proteins of the invention have increased stability and improved half-life as compared to known therapeutic agents used in reproductive, and/or FSH, therapy. The fusion proteins of the invention can be administered parenterally or non-invasively. While current FSH therapeutics are generally administered by subcutaneous or intramuscular injections, the fusion proteins of the invention can be administered by less invasive means, such as oral administration, nasal administration, or pulmonary administration. Current therapy requires daily injections, whereas the present invention may provide for less frequent parenteral, oral, or pulmonary dosing.

B. Fusion Proteins

The invention relates to fusion proteins of heterodimeric FSH wherein the alpha and beta subunits of FSH are each conjugated to an FcRn binding partner or to an Fc fragment. More specifically, the invention in one embodiment provides fusion proteins having two polypeptide chains, one chain having at least αFSH, linked directly or indirectly through an optional linker, to an FcRn binding partner, and the second chain having βFSH, also linked directly or indirectly through an optional linker to an FcRn binding partner. In the subject fusions, the head of αFSH is aligned with the head of βFSH and the tails of the respective FcRn binding partners are aligned. In one embodiment of the invention, there is a linker between the FSH subunits and the respective FcRn binding partners.

In another embodiment of the invention, the fusion protein comprises two polypeptide chains of the formula αFSH-L-Fc:βFSH-L-Fc wherein αFSH is the alpha subunit of FSH, βFSH is the beta subunit of FSH, L is a linker or direct bond, Fc is an Fc fragment of an immunoglobulin, and the colon (:) represents an association between the two polypeptide chains of the fusion. In this embodiment, the carboxy termini of αFSH and βFSH are linked either directly or indirectly through L to the amino terminus of the respective Fc and the head of αFSH is aligned with the head of βFSH and the tails of each of the respective Fc fragments are aligned.

In an alternative embodiment, the fusion protein comprises two polypeptide chains of the formula Fc-L-αFSH:Fc-L-βFSH wherein all aspects of the fusion are as described above for the preceding embodiment, excepting that the amino termini of αFSH and βFSH are linked either directly or indirectly through L to the carboxy terminus of the respective Fc.

The association between the two polypeptide chains can be the result of an association between the alpha and beta subunits of FSH and/or the result of an association between the Fc fragments or FcRn binding partners. For example, in the instance of an association of the alpha and beta subunits of FSH, the interaction may be a non-covalent interaction, e.g., an ionic interaction, a hydrophobic or hydrophilic interaction, a Van der Waals interaction, and/or a hydrogen bond, e.g., leucine zipper. Non-covalent association or interaction can involve interdigitation of amphiphilic peptides such as, but not limited to, alpha helices, charge-charge interactions of amino acids bearing opposite charges, such as, but not limited to, lysine and aspartic acid, arginine and glutamic acid. In one embodiment the non-covalent association or interaction involves a leucine zipper comprising a peptide having several repeating amino acids in which every seventh amino acid is a leucine residue. (See, e.g., Branden et al. (1991) *Introduction To Protein Structure*, Garland Publishing, New York). In the case of interactions between the Fc fragments, generally, they will be covalent bonds, and are generally one or two disulfide bonds as is found in many of the Fc fragments of immunoglobulins. Therefore, in certain embodiments of the invention, there exists at least one disulfide bridge between the Fc fragments of the subject fusion.

In certain embodiments of the invention, conjugated to the subject fusion, or one polypeptide chain thereof, can be a second linker or alternatively a tag that can be used to facilitate purification of the fusion protein, e.g., a FLAG tag, a histidine tag (see Example 1), a GST tag, a maltose binding protein tag, or others known in the art.

1. Fusion Protein Variants

Derivatives and analogs of the fusion proteins of the invention, antibodies against the fusion proteins of the invention, and antibodies against binding partners of the fusion proteins of the invention are all contemplated, and can be made by altering their amino acid sequences by substitutions, additions, and/or deletions/truncations or by introducing chemical modifications that result in functionally equivalent molecules. It will be understood by one of ordinary skill in the art that certain amino acids in a sequence of any protein may be substituted for other amino acids without adversely affecting the activity of the protein.

Various changes may be made in the amino acid sequences of the fusion proteins of the invention or DNA sequences encoding therefor without appreciable loss of their biological activity, function, or utility. Derivatives, analogs, or mutants resulting from such changes and the use of such derivatives is within the scope of the present invention. In a specific embodiment, the derivative is functionally active, i.e., capable of exhibiting one or more activities associated with the fusion proteins of the invention, e.g., increased fertility, increased egg production, increased spermatogenesis.

Substitutes for an amino acid within the sequence may be selected from other members of the class to which the amino acid belongs (see Table 1). Furthermore, various amino acids are commonly substituted with neutral amino acids, e.g., alanine, leucine, isoleucine, valine, proline, phenylalanine, tryptophan, and methionine (see, e.g., MacLennan et al. (1998) *Acta Physiol. Scand. Suppl.* 643:55-67; Sasaki et al. (1998) *Adv. Biophys.* 35:1-24).

TABLE 1

Amino Acids and Their Substitutions

| Original Residues | Exemplary Substitutions | Typical Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

2. Heterodimeric Follicle Stimulating Hormone

The fusion proteins of the instant invention include heterodimeric FSH (alternatively referred to as "FSH heterodimer"). Recombinant heterodimeric FSH is described in U.S. Pat. No. 5,767,251. In an embodiment of the invention the FSH is human FSH (hFSH). Exemplary libraries containing the beta and/or alpha subunits of FSH are described in the ensuing Examples, and nucleotide sequences for alpha and beta subunits of human FSH are publicly available through GenBank as accession numbers NM_000735 and NM_000510, respectively.

3. Immunoglobulins

Immunoglobulins are comprised of four protein chains that associate covalently—two heavy chains and two light chains. Each chain is further comprised of one variable region and one constant region. Depending upon the immunoglobulin isotype (i.e., IgG, IgM, IgA, IgD, IgE), the heavy chain constant region is comprised of 3 or 4 constant region domains (e.g., CH1, CH2, CH3, CH4). Some isotypes can also include a hinge region (e.g., IgG).

In certain embodiments, the fusion proteins of the invention are the alpha and beta subunits of FSH each respectively conjugated to a neonatal Fc receptor (FcRn) binding partner. An FcRn binding partner is any molecule that can be specifically bound by the FcRn receptor with consequent active transport by the FcRn receptor of the FcRn binding partner. The FcRn receptor has been isolated from several mammalian species including humans. The sequences of the human FcRn, rat FcRn, monkey FcRn, and mouse FcRn are known (Story et al. (1994) *J. Exp. Med.* 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,030,613 and 6,086,875) including lung and intestinal epithelium (Israel et al. (1997) *Immunology* 92:69), renal proximal tubular epithelium (Kobayashi et al. (2002) *Am. J. Physiol. Renal Physiol.* 282:F358), as well as nasal epithelium, vaginal surfaces, and biliary tree surfaces.

An FcRn binding partner contains a ligand for the FcRn which mimics that portion of the Fc domain of IgG which binds the FcRn (i.e., an Fc, an Fc domain, Fc fragment, Fc fragment homolog, and Fc mimetic). Thus the FcRn binding partners of the present invention encompass any molecule that can be specifically bound by the FcRn receptor including whole IgG, the Fc fragment of IgG, and other fragments that include the complete binding region of the FcRn receptor. In certain embodiments, the FcRn binding partner is non-specific IgG or an FcRn-binding fragment of IgG. Most typically the FcRn binding partner corresponds to the Fc fragment of IgG, i.e., Fcγ. The Fcγ can be native or it can be modified so that it has a higher affinity for FcRn than native Fcγ. Such modification can include substitution of certain amino acid residues involved in contact with FcRn. The region of the Fc portion of IgG that binds to the FcRn receptor has been described based on X-ray crystallography (Burmeister et al. (1994) *Nature* 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, *Sequences of Proteins of Immunological Interest*, U.S. Department of Public Health, Bethesda, Md. The Fcγ can be modified so that it has a longer circulating half-life than native Fcγ. Such modification can include substitution of certain amino acid residues involved in interaction with Fc receptors other than FcRn, substitution of certain amino acid residues involved in glycosylation, and the like. Specific exemplary modifications are described hereinbelow.

In other embodiments of the invention the FcRn binding partner is an Fc fragment, meaning an immunoglobulin heavy chain constant region, portion thereof, or variant thereof. It can be, or be derived from, an immunoglobulin heavy chain constant region, including, but not limited to a human immunoglobulin heavy chain constant region, a non-human primate immunoglobulin heavy chain constant region, a bovine immunoglobulin heavy chain constant region, a porcine immunoglobulin heavy chain constant region, a murine immunoglobulin heavy chain constant region, an ovine immunoglobulin heavy chain constant region, or a rat immunoglobulin heavy chain constant region.

The Fc fragments or FcRn binding partners of the invention can include the entire heavy chain constant region, or a fragment or analog thereof. A heavy chain constant region can comprise a CH1 domain, a CH2 domain, a CH3 domain, a CH4 domain, and/or a hinge region. In one embodiment a heavy chain constant region can comprise a hinge region, a CH2 domain, and a CH3 domain.

The immunoglobulin can be produced recombinantly or synthetically. The immunoglobulin can be isolated from a cDNA library. The immunoglobulin can be isolated from a phage library (see McCafferty et al. (1990) *Nature* 348:552). The immunoglobulin can be obtained by gene shuffling of known sequences (Mark et al. (1992) *Bio/Technol.* 10:779).

The immunoglobulin can be isolated by in vivo recombination (Waterhouse et al. (1993) *Nucl. Acid Res.* 21:2265). The immunoglobulin can be a humanized immunoglobulin (Jones et al. (1986) *Nature* 332:323).

An Fc fragment can be comprised of the CH2 and CH3 domains of an immunoglobulin and optionally the hinge region of the immunoglobulin. The Fc fragment can be of an IgG, an IgA, an IgM, an IgD, an IgE. In one embodiment, the immunoglobulin is an IgG, IgA or IgD. In one embodiment the Fc fragment is an Fc fragment of IgG. The Fc fragment can be the Fc fragment of an IgG1, an IgG2, an IgG3 or an IgG4. In one embodiment, the immunoglobulin is human IgG1. In yet another embodiment, the immunoglobulin is IgG2. In another embodiment, the Fc fragment is comprised of the amino acid sequence from amino acid number 145 to amino acid number 371 of SEQ ID NO:4, or an analog thereof. In one embodiment the Fc fragment is encoded by a nucleic acid sequence comprising nucleotides 446 to 1126 of SEQ ID NO.3.

The FcRn binding partners or Fc fragments can include an Fc variant. Fc variant refers to a molecule or sequence that is modified from a native Fc but still comprises a binding site for the salvage receptor, FcRn (WO 97/34631). Native refers to an Fc that has not been modified by a human. WO 96/32478 describes exemplary Fc variants, as well as interaction with the salvage receptor. Thus, the term "Fc variant" in one embodiment comprises a molecule or sequence that is humanized from a non-human native Fc. Furthermore, a native Fc comprises sites that may be removed because they provide structural features or biological activity that are not required for the fusion molecules of the present invention. Thus, Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine, other amino acids may be substituted for the wildtype amino acids at the positions specified above. Mutations may be introduced singly into Fc, giving rise to more than one hundred FcRn binding partners distinct from native Fc. Additionally, combinations of two, three, or more of these individual mutations may be introduced together, giving rise to hundreds more FcRn binding partners.

Certain of the above mutations may confer new functionality upon the FcRn binding partner. For example, one embodiment incorporates N297A, removing a highly conserved N-glycosylation site. The effect of this mutation is to reduce binding to immune effector cells and potentially decrease immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. (1995) *Transplantation* 60:847; Friend et al. (1999) *Transplantation* 68:1632; Shields et al. (1995) *J. Biol. Chem.* 276:6591). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" with the corresponding sequence from IgG2 "PVA" (with one amino acid deletion). It has been shown that FcγRI, FcγRII, and FcγRIII, which mediate various effector functions, will not bind to IgG1 when such mutations have been introduced (Ward and Ghetie (1995) *Therapeutic Immunology* 2:77 and Armour et al. (1999) *Eur. J. Immunol.* 29:2613). As a further example of new functionality arising from mutations described above, affinity for FcRn may be increased beyond that of wildtype in some instances. This increased affinity may reflect an increased "on" rate, a decreased "off" rate, or both an increased "on" rate and a decreased "off" rate. Mutations believed to impart an increased affinity for FcRn include T256A, T307A, E380A, and N434A (Shields et al. (2001) *J. Biol. Chem.* 276:6591).

In certain embodiments the FcRn binding partner or Fc fragment is a polypeptide including the sequence PKNSSMISNTP (SEQ ID NO:11) and optionally further including a sequence selected from HQSLGTQ (SEQ ID NO:12), HQNLSDGK (SEQ ID NO:13), HQNISDGK (SEQ ID NO:14), or VISSHLGQ (SEQ ID NO:15; U.S. Pat. No. 5,739, 277).

Two FcRn receptors can bind a single Fc molecule. Crystallographic data suggest that each FcRn molecule binds a single polypeptide of the Fc homodimer. Linking the FcRn binding partner, e.g., an Fc fragment of an IgG, to heterodimeric FSH thus provides a means of delivering FSH orally, nasally, via an ocular route, or via a pulmonary route. For delivery nasally or via a pulmonary route, in one embodiment the fusion protein is administered as an aerosol.

The skilled artisan will understand that portions of an immunoglobulin constant region for use in the fusion protein of the invention can include mutants or analogs thereof, or can include chemically modified immunoglobulin constant regions or fragments thereof (e.g., pegylation) (see, e.g., Aslam and Dent (1998) *Bioconjugation: Protein Coupling Techniques for the Biomedical Sciences*, Macmillan Reference, London). In one instance a mutant can provide for enhanced binding of an FcRn binding partner for the FcRn. Also contemplated for use in the fusion protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display (See, e.g., McCafferty et al. (1990) *Nature* 348:552; Kang et al. (1991) *Proc. Natl. Acad. Sci. USA* 88:4363; EP 0 589 877 B1).

4. Optional Linkers

The fusion protein of the invention can optionally comprise at least one linker molecule. In one embodiment, the linker is comprised of amino acids linked together by peptide bonds, wherein the amino acids are selected from the twenty naturally occurring amino acids. In various embodiments the linker can comprise 1-5 amino acids, 1-10 amino acids, 1-20 amino acids, 10-50 amino acids, 50-100 amino acids, or 100-200 amino acids. In one embodiment the amino acids are selected from glycine, alanine, proline, asparagine, glutamine, and lysine. In one embodiment a linker is made up of a majority of amino acids that are sterically unhindered, such as glycine and alanine.

The linker in one embodiment can comprise the sequence Gn (equivalently, -(Gly)n-). The linker can in one embodiment comprise the sequence (GGS)n or (GGGGS)n. In each instance, n may be an integer, such as 1, 2, 3, 4, 5, 6, 7, 8, 9, or 10. Examples of linkers include, but are not limited to, GGG, SGGSGGS (SEQ ID NO:16), GGSGGSGGSGGSGGG (SEQ ID NO:17), GGSGGSGGSGGSGGSGGS (SEQ ID NO:18), and GGGGSGGGGSGGGGS (SEQ ID NO:10; GS15).

In one embodiment the linker is an 8-amino acid linker EFAGAAAV (SEQ ID NO:9).

Non-peptide linkers are also possible. For example, alkyl linkers such as —NH—(CH2)m-C(O)—, wherein m=2-20, could be used. These alkyl linkers may further be substituted by any non-sterically hindering group such as lower alkyl (e.g., C1 to C6) lower acyl, halogen (e.g., Cl, Br), CN, NH2, phenyl, etc. An exemplary non-peptide linker is a PEG linker. Additional linkers useful according to the present invention are described in U.S. Pat. No. 6,660,843.

C. Nucleic Acid Constructs

The invention also relates to nucleic acid constructs encoding the heterodimer FSH-Fc fusion proteins of the invention. Each nucleic acid sequence comprises a first nucleic acid sequence encoding one subunit of FSH, for example the alpha subunit of FSH, operatively linked to a second nucleic acid sequence encoding at least an Fc fragment or FcRn binding partner. In one embodiment a first nucleic acid sequence encoding the alpha subunit of FSH is operatively linked to a second nucleic acid sequence encoding at least an Fc fragment or FcRn binding partner, and a third nucleic acid sequence encoding the beta subunit of FSH is operatively linked to a fourth nucleic acid sequence encoding at least an Fc fragment or FcRn binding partner (second and fourth nucleic acid sequences generally being identical). The nucleic acids of the invention thus pertain to nucleic acid constructs encoding both polypeptide chains of the subject fusions. The nucleic acids of the invention can be present in a single nucleic acid construct or in separate constructs. The nucleic acid sequence can also include additional sequences or elements known in the art (e.g., promoters, enhancers, poly A sequences, signal sequence). The nucleic acid sequence can optionally include a sequence encoding a linker placed between the nucleic acid sequence encoding the alpha or beta subunits of FSH and the nucleic acid sequence encoding the Fc fragment or FcRn binding partner.

In one embodiment, each nucleic acid construct is comprised of DNA. In another embodiment, each nucleic acid construct is comprised of RNA. The nucleic acid construct can be a vector, e.g., a viral vector or a plasmid. Examples of viral vectors include, but are not limited to adenovirus vector, an adeno associated virus vector, and murine leukemia virus vector. Examples of plasmids include but are not limited to, e.g., pUC, pGEX, pcDNA3, pcDNA4, pcDNA6, and pED.dC. In certain embodiments the plasmid is an expression plasmid.

In one embodiment, the nucleic acid construct comprises the nucleic acid sequences of SEQ ID NO:1 and SEQ ID NO:3.

Due to the known degeneracy of the genetic code, wherein more than one codon can encode the same amino acid, a DNA sequence can vary from that shown in SEQ ID NOS:1 and 3 and still encode a polypeptide having the amino acid sequence of SEQ ID NOS:2 and 4, respectively. Such variant DNA sequences can result from silent mutations (e.g., occurring during PCR amplification), or can be the product of deliberate mutagenesis of a native sequence. The invention thus provides isolated DNA sequences encoding polypeptides of the invention, selected from: (a) DNA comprising the nucleotide sequences of SEQ ID NO:1 and 3; (b) DNA encoding the polypeptide of SEQ ID NO:2 and 4; (c) DNA capable of hybridization to a DNA of (a) or (b) under conditions of moderate stringency and which encodes polypeptides of the invention; (d) DNA capable of hybridization to a DNA of (a) or (b) under conditions of high stringency and which encodes polypeptides of the invention, and (e) DNA which is degenerate as a result of the genetic code to a DNA defined in (a), (b), (c), or (d) and which encode polypeptides of the invention. Of course, polypeptides encoded by such DNA sequences are encompassed by the invention.

In another embodiment, the nucleic acid molecules of the invention also comprise nucleotide sequences that are at least 80% identical to a native sequence. Also contemplated are embodiments in which a nucleic acid molecule comprises a sequence that is at least 90% identical, at least 95% identical, at least 98% identical, at least 99% identical, or at least 99.9% identical to a native sequence. In this context the native sequence can refer to the sequence of Fc, αFSH, or βFSH, as they may be found in nature. The percent identity may be determined by visual inspection and mathematical calculation. Alternatively, the percent identity of two nucleic acid sequences can be determined by comparing sequence information using the GAP computer program, version 6.0 described by Devereux et al. (1984) *Nucl. Acids Res.* 12:387, and available from the University of Wisconsin Genetics Computer Group. The preferred default parameters for the GAP program include: (1) a unary comparison matrix (containing a value of 1 for identities and 0 for non identities) for nucleotides, and the weighted comparison matrix of Gribskov and Burgess (1986) *Nucl. Acids Res.* 14:6745, as described by Schwartz and Dayhoff, eds., 1979, *Atlas of Protein Sequence and Structure*, National Biomedical Research Foundation, pp. 353-358; (2) a penalty of 3.0 for each gap and an additional 0.10 penalty for each symbol in each gap; and (3) no penalty for end gaps. Other programs used by one skilled in the art of sequence comparison may also be used.

D. Synthesis of Fusion Proteins

Fusion proteins of the subject invention can be synthesized using techniques well known in the art. For example fusion proteins of the invention can be synthesized recombinantly in cells (see, e.g., Sambrook et al. (1989) *Molecular Cloning A Laboratory Manual*, Cold Spring Harbor Laboratory, N.Y., and Ausubel et al. (1989) *Current Protocols in Molecular Biology*, Greene Publishing Associates and Wiley Interscience, N.Y.).

DNA sequences encoding immunoglobulins, or fragments thereof, or FSH, or fragments thereof, may be cloned from a variety of genomic, cDNA, or RNA libraries known in the art. The techniques for isolating such DNA sequences using probe-based methods are conventional techniques and are well known to those skilled in the art. Probes for isolating such DNA sequences may be based on published DNA sequences (see, for example, Hieter et al. (1980) *Cell* 22: 197-207). The polymerase chain reaction (PCR) method disclosed by Mullis et al. (U.S. Pat. No. 4,683,195) and Mullis (U.S. Pat. No. 4,683,202) may be used. The choice of library and selection of probes for the isolation of such DNA sequences is within the level of ordinary skill in the art. Alternatively, DNA sequences encoding immunoglobulins, or fragments thereof, or FSH can be obtained from vectors known in the art to contain immunoglobulins, or fragments thereof, or FSH.

For recombinant production, a polynucleotide sequence encoding the fusion protein is inserted into an appropriate expression vehicle, i.e., a vector which contains the necessary elements for the transcription and translation of the inserted coding sequence, or in the case of an RNA viral vector, the necessary elements for replication and translation. The nucleic acid encoding the fusion protein is inserted into the vector in proper reading frame.

The expression vehicle is then transfected or otherwise introduced into a suitable target cell which will express the protein, e.g., a fusion protein. Transfection techniques known in the art include, but are not limited to, liposomal transfection, calcium phosphate precipitation (Wigler et al. (1978) *Cell* 14:725), and electroporation (Neumann et al. (1982) *EMBO J.* 1:841). A variety of host-expression vector systems may be utilized to express the fusion proteins described herein in eukaryotic cells. In one embodiment, the eukaryotic cell is an animal cell, including mammalian cells (e.g., CHO, BHK, COS, HeLa cells). When the fusion protein is expressed in a eukaryotic cell, the DNA encoding the fusion protein may also code for a signal sequence that will permit the fusion protein to be secreted. One skilled in the art will understand that while the protein is translated the signal sequence is cleaved by the cell to form the mature fusion protein. Various signal sequences are known in the art, e.g., mouse Igκ light chain signal sequence. Alternatively, where a signal sequence is not included, the fusion protein can be recovered by lysing the cells.

The fusion protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. (1985) *Proc. Natl. Acad. Sci. USA* 82:4438). Methods of producing transgenic animals are known in the art, including transgenics that produce immunoglobulin molecules (Wagner et al. (1981) *Proc. Natl. Acad. Sci. USA* 78:6376; McKnight et al. (1983) *Cell* 34:335; Brinster et al. (1983) *Nature* 306:332; Ritchie et al. (1984) *Nature* 312:517; Baldassarre et al. (2003) *Theriogenology* 59:831; Robl et al. (2003) *Theriogenology* 59:107; Malassagne et al. (2003) *Xenotransplantation* 10(3):267).

The expression vectors can encode for tags that permit for easy purification or identification of the recombinantly produced protein. Examples include, but are not limited to, vector pUR278 (Ruther et al. (1983) *EMBO J.* 2:1791) in which the fusion protein described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e.g., PreCission Protease™ (Pharmacia, Peapack, N.J.) for easy removal of the tag after purification. Additional tags include FLAG, a histidine tag (see Example 1 below) a maltose binding protein tag, and others known to those of skill in the art.

To increase efficiency of production, the polynucleotide can be designed to encode multiple units of the fusion protein of the invention separated by enzymatic cleavage sites. The resulting polypeptide can be cleaved (e.g., by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript, e.g., by an internal ribosome entry site (IRES). Thus, the polycistronic construct directs the transcription of a single, large polycistronic mRNA which, in turn, directs the translation of multiple, individual polypeptides. This approach eliminates the production and enzymatic processing of polyproteins and may significantly increase yield of a polypeptide driven by a single promoter.

Vectors used in transformation and transfection will usually contain a selectable marker used to identify transformants and transfectants. In bacterial systems this can include an antibiotic resistance gene such as ampicillin, blasticidin or kanamycin. Selectable markers for use in cultured mammalian cells include genes that confer resistance to drugs, such as neomycin, hygromycin, blasticidin, geneticin, zeocin, and methotrexate. The selectable marker may be an amplifiable selectable marker. One amplifiable selectable marker is the dihydrofolate reductase gene (DHFR gene) or the cDNA thereof (Simonsen and Levinson (1983) *Proc. Natl. Acad. Sci. USA* 80:2495). Selectable markers are reviewed by Thilly (1986) *Mammalian Cell Technology*, Butterworth Publishers, Stoneham, Mass., and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrplac hybrid promoter) and the like may be used; when cloning in insect cell systems, promoters such as the baculovirus polyhedron promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5 K promoter, the CMV promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the fusion proteins of the invention may be driven by any of a number of promoters. For example, viral promoters such as the 35S RNA and 19S RNA promoters of CaMV (Brisson et al. (1984) *Nature* 310:511-514), or the coat protein promoter of TMV (Takamatsu et al. (1987) *EMBO J.* 6:307-311) may be used; alternatively, plant promoters such as the small subunit of RUBISCO (Coruzzi et al. (1984) *EMBO J.* 3:1671-1680; Broglie et al. (1984) *Science* 224: 838-843) or heat shock promoters, e.g., soybean hsp17.5-E or hsp17.3-B (Gurley et al. (1986) *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach (1988) *Methods for Plant Molecular Biology*, Academic Press, NY, Section VIII, pp. 421-463; and Grierson & Corey (1988) *Plant Molecular Biology*, 2d Ed., Blackie, London, Ch. 7-9.

In one insect expression system that may be used to produce the fusion proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed (see, e.g., Smith et al. (1983) *J. Virol.* 46:584; U.S. Pat. No. 4,215,051). Further examples of this expression system may be found in Ausubel et al., eds (1989) *Current Protocols in Molecular Biology*, Vol. 2, Greene Publish. Assoc. & Wiley Interscience.

Another system which can be used to express the fusion proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral-based expression systems may be utilized. In cases where an adenovirus is used as an expression vector, a coding sequence may be ligated to an adenovirus transcription/translation control complex, e.g., the late promoter and tripartite leader sequence. This fusion gene may then be inserted in the adenovirus genome by in vitro or in vivo recombination. Insertion in a non-essential region of the viral genome (e.g. region E1 or E3) will result in a recombinant virus that is viable and capable of expressing a polypeptide peptide in infected hosts (see, e.g., Logan & Shenk (1984) *Proc. Natl. Acad. Sci. USA* 81:3655-3659). Alternatively, the vaccinia 7.5 K promoter may be used (see, e.g., Mackett et al. (1982) *Proc. Natl. Acad. Sci. USA* 79:7415; Mackett et al. (1984) *J. Virol.* 49:857; Panicali et al. (1982) *Proc. Natl. Acad. Sci. USA* 79:4927).

Host cells containing DNA constructs of the fusion protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. For example, the media can contain bovine calf serum or fetal calf serum. The growth medium will generally select for cells containing the DNA construct by, for example, drug selection or deficiency in an essential nutrient, which is complemented by the selectable marker on the DNA construct or co-transfected with the DNA construct. Cultured mammalian cells are generally grown in commercially available serum-containing or serum-free media (e.g. MEM, DMEM). Selection of a medium appropriate for the particular cell line used is within the level of ordinary skill in the art.

The recombinantly produced fusion protein of the invention can be isolated from the culture media using procedures well-established in the art (e.g., affinity chromatography, size exclusion chromatography, ion exchange chromatography). The fusion protein of the invention can be isolated from the culture media by column chromatography, e.g., a protein A column, or by ion exchange chromatography. The culture medium from appropriately grown transformed or transfected host cells is separated from the cell material, and the presence of fusion proteins is demonstrated. One method of detecting the fusion proteins, for example, is by the binding of the fusion proteins or portions of the fusion proteins to a specific antibody recognizing the fusion protein of the invention (e.g., an anti-Fc antibody). An anti-fusion protein antibody may be a monoclonal or polyclonal antibody raised against the fusion protein in question. For example, the fusion protein can contain a portion of an immunoglobulin constant region. Antibodies recognizing the constant region of many immunoglobulins are known in the art and are commercially available. An antibody can be used to perform an ELISA or a western blot to detect the presence of the fusion protein of the invention.

E. Methods of Using Fusion Proteins

The fusion proteins of the invention have many uses as will be recognized by one skilled in the art, including, but not limited to methods of treating a subject having a reproductive disorder and methods of treating a subject in need of increased fertility and/or FSH therapy for treatment of an FSH abnormality.

1. Methods of Treating a Subject Having a Reproductive Disorder

The invention relates to a method of treating a subject having a reproductive disorder or FSH abnormality. Such abnormalities are described, for example, in *Harrison's Principles of Internal Medicine*, 15th Ed., E. Braunwald et al., eds, McGraw-Hill, New York, 2001. Thus the invention provides a method for treating a disease state responsive to FSH therapy by administering a fusion protein provided herein. Such therapies generally relate to infertility or a reproductive disorder. Accordingly, the invention provides a method of increasing a subject's fertility by administering an amount of the present fusion protein sufficient to enhance the subject's fertility. In one embodiment, this method is used to enhance the efficacy of in vitro fertilization protocols. For example, the subject fusion proteins of the instant invention can enhance the success of in vitro fertilization by stimulating follicular maturation and egg production in a patient. The invention also provides a method of increasing a subject's egg production or a method of increasing spermatogenesis, by administering to a subject an effective amount of the instant fusion protein to obtain the desired increase.

As used herein, a subject can be a mammal, for example, a human, a non-human primate, a horse, a sheep, a cow, a pig, a dog, a cat, or a rodent. In one embodiment, the subject is a human.

In one embodiment of the invention is provided a method of increasing the half-life of heterodimeric FSH. By way of this embodiment, FSH may be administered to a subject less frequently than current methods allow. For example, an FSH fusion of the invention may be administered only one, two, or three times over an 8 to 12 day cycle.

There are numerous assays available by which to determine the activity of a given heterodimeric FSH-Fc construct of the invention and its usefulness in the above-described methods of treatment. Standard assays are listed hereinbelow and some are described in detail, with modifications to certain of the protocols, in the ensuing Examples.

Standard in vitro assays include: rat Sertoli cell bioassays to measure estrogen production (Dorrington, J H and Armstrong, D T (1975) *Proc. Natl. Acad. Sci. USA* 72:2677); rat Sertoli cell bioassays to measure aromatase activity (Padmanabhan V, Chappel S C, Beitins, I Z (1987) *Endocrinology* 121:1089-1098); rat granulosa cell bioassay to measure aromatase activity (Jia X C and Hsueh A J W (1986) *Endocrinology* 119:1570-1577; Dahl K D, et al. (1987) *J Clin Endocrinol Metab* 64:486-493); and FSH receptor binding/cAMP production assays (Tano M, Minegishi T, Nakamura K, Karino S, Ibuki Y (1995) *Fertil Steril* 64:1120-1124).

Standard in vivo assays include: in rodents, ovarian weight gain, known as the Steelman Pohley assay (Steelman S L and Pohley F M (1953) *Endocrinology* 53:604-616) and testis weight gain (Meachem S J, McLachlan R I, deKretser D M, Robertson D M, Wreford N G (1996) *Biol Reprod* 54:36-44); in non-human primates, estrogen production (Klein J et al. (2002) *Fertil Steril* 77:1248-1255) and inhibin levels (Weinbauer G F et al. (1994) *J Endocrinol* 141:113-121); and in humans, serum estrogen, serum inhibin and follicle size/number (Porchet H C et al. (1994) *Fertil Steril* 61:687-695).

The fusion protein of the invention can be administered intravenously, subcutaneously, intra-muscularly, or via any mucosal surface, e.g., orally, sublingually, buccally, nasally, rectally, vaginally or via pulmonary route. The fusion protein can be implanted within or linked to a biopolymer solid support that allows for the slow release of the fusion protein. In one embodiment the fusion protein is administered parenterally. In one embodiment the fusion protein is administered orally. In one embodiment the fusion protein is administered via a pulmonary route.

The dose of the fusion protein of the invention will vary depending on the subject and upon the particular route of administration used. Dosages can range from 0.1 to 100,000 µg/kg body weight. In one embodiment, the dosing range is 0.1-1,000 µg/kg. The protein can be administered continuously or at specific timed intervals. In vitro assays may be employed to determine optimal dose ranges and/or schedules for administration. In vitro assays that measure FSH activity are known in the art as described in detail above. Additionally, effective doses may be extrapolated from dose-response curves obtained from animal models, e.g., non-human primates.

The invention also relates to a pharmaceutical composition comprising the subject fusion protein and a pharmaceutically acceptable carrier or excipients. Examples of suitable pharmaceutical carriers are described in *Remington's Pharmaceutical Sciences* by E. W. Martin. Examples of excipients can include starch, glucose, lactose, sucrose, gelatin, human serum albumin, detergent (e.g. Tween-20), malt, rice, flour, chalk, silica gel, sodium stearate, glycerol monostearate, talc, sodium chloride, dried skim milk, glycerol, polyethylene glycol, propylene glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid, for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch. Aerosols containing fusion proteins of the subject invention may be prepared as described in U.S. 2003/023553 A1 which is incorporated herein by reference.

The pharmaceutical composition can be formulated for parenteral (e.g. intravenous or intramuscular) administration by injection or infusion. Formulations for injection or infusion can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen-free water.

The pharmaceutical composition can also be formulated for rectal administration as a suppository or retention enema, e.g., containing conventional suppository bases such as cocoa butter or other glycerides.

EXAMPLES

Example 1

Construction of Single-Chain FSH-Fc and Heterodimer FSH-Fc Fusion Molecules

For single-chain FSH-Fc constructs, FSH beta was isolated with its native signal sequence from a human pituitary mRNA library (Clontech, Palo Alto, Calif.) using standard reverse transcriptase-polymerase chain reaction (RT-PCR) techniques. FSH alpha was isolated from the same human pituitary mRNA library but without its signal sequence. The two FSH subunits were ligated to form a contiguous FSH beta-FSH alpha fusion without a 3' termination codon. The Fc fragment of human IgG$_1$ (hinge, CH2 and CH3 domains; amino acids 221-447, EU numbering) was prepared as previously described (U.S. 2003/0235536 A1) using standard polymerase chain reaction (PCR) techniques. Primers were designed to create an 8-amino acid linker sequence (EFA-GAAAV; SEQ ID NO:9) on the 5' end of the Fc fragment. The human Fc PCR fragment was cloned into the mammalian expression vector, pED.dC (Genetics Institute, Cambridge, Mass.) that contains an adenovirus major late promoter and a mouse dihydrofolate reductase (dhfr) gene as a selectable marker. The single-chain FSH molecule was then cloned into pED.dC containing the human Fc sequence, thus creating a fusion molecule of FSH beta-FSH alpha-Fc with an eight amino acid linker connecting the FSH subunits to the Fc (FIG. 1a).

Figure 1B:
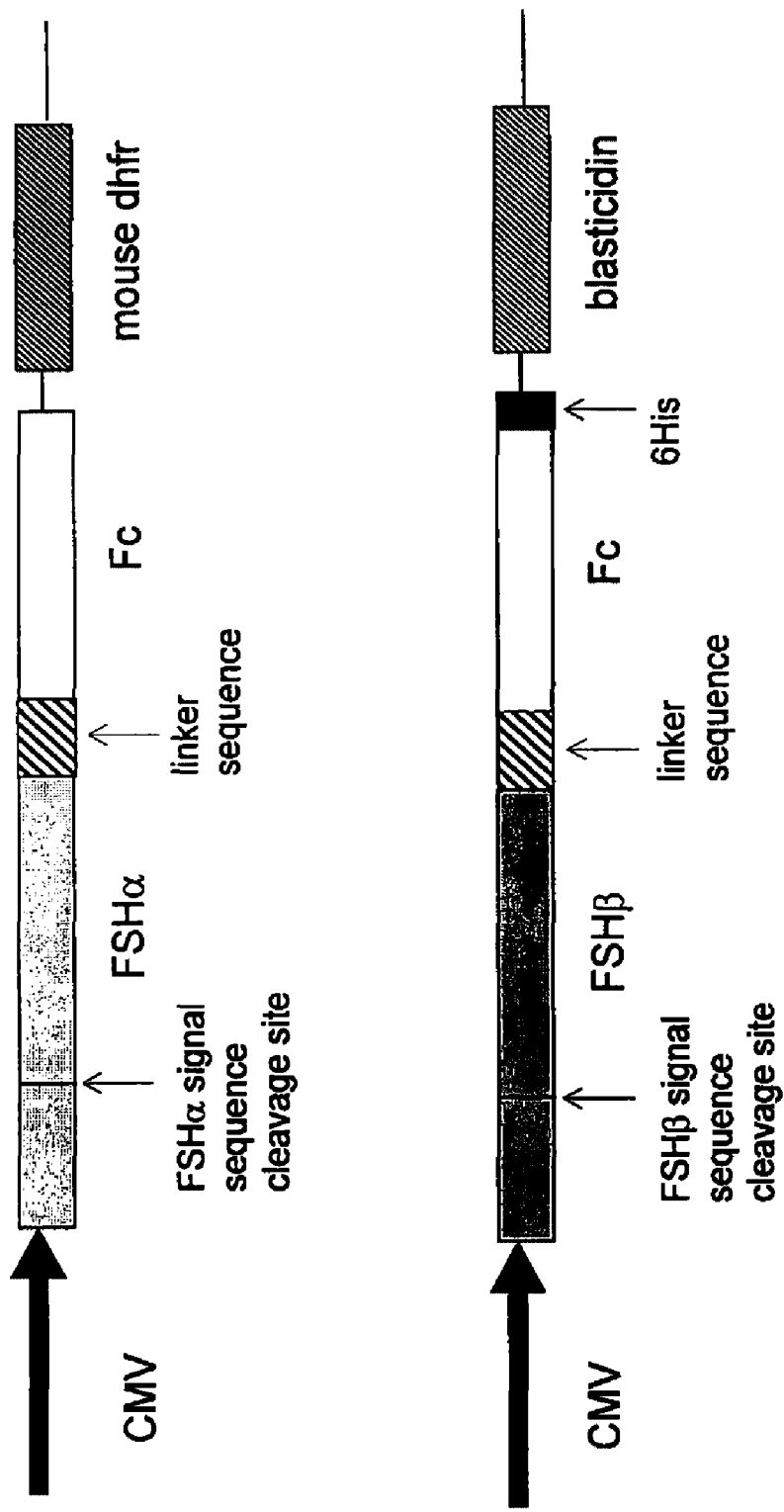

For heterodimer FSH-Fc constructs, both FSH alpha and FSH beta subunits were isolated from the same human pituitary mRNA library, each with its native signal sequence. The 8-amino acid linker sequence from the Fc in pED.dC was replaced by a fifteen amino acid linker sequence, GS15 ((GGGGS)₃; SEQ ID NO:10). The adenovirus major late promoter in pED.dC was replaced by a cytomegalovirus (CMV) promoter using standard PCR techniques to create restriction sites on the 5' and 3' ends of the CMV promoter that allowed excision of the adenovirus major late promoter and replacement with the CMV promoter. The template for the PCR reaction was pcDNA6/V5-His (Invitrogen, Carlsbad, Calif.), a mammalian expression vector containing a CMV promoter and blasticidin gene for selection purposes. The GS15 linker/Fc fragment from pED.dC was also ligated into pcDNA6/V5-His to create a second vector with a unique selection marker. FSH alpha was then cloned into the GS15-Fc-pED.dC vector, while FSH beta was cloned into the GS15-Fc-pcDNA6/V5-His. For purification purposes a 6H is tag sequence was fused onto the 3' end of the Fc in FSH beta-Fc in pcDNA6/V5-His (FIG. 1b).

Resulting full length nucleotide coding and amino acid sequences for FSH alpha-Fc are provided as SEQ ID NO:1 and SEQ ID NO:2, respectively.

SEQ ID NO: 1
cctgcaggccacc<u>atggattactacagaaaatatgcagctatctttctgg tcacattgtcggtgtttctgcatgttctccattccg</u>ctcctgatgtgcag gattgcccagaatgcacgctacaggaaaacccattcttctcccagccggg tgccccaatacttcagtgcatgggctgctgcttctctagagcatatccca ctccactaaggtccaagaagacgatgttggtccaaaagaacgtcacctca gagtccacttgctgtgtagctaaatcatataacagggtcacagtaatggg gggtttcaaagtggagaaccacacggcgtgccactgcagtacttgttatt atcacaaatctggtggaggcggatccggtggaggcgggtccggcggtgga gggagcgacaaaactcacacgtgcccgccgtgcccagctccggaactgct gggcggaccgtcagtcttcctcttccccccaaaacccaaggacaccctca tgatctcccggacccctgaggtcacatgcgtggtggtggacgtgagccac gaagaccctgaggtcaagttcaactggtacgtggacggcgtggaggtgca taatgccaagacaaagccgcgggaggagcagtacaacagcacgtaccgtg tggtcagcgtcctcaccgtcctgcaccaggactggctgaatggcaaggag tacaagtgcaaggtctccaacaaagccctcccagcccccatcgagaaaac catctccaaagccaaagggcagccccgagaaccacaggtgtacaccctgc ccccatcccgggatgagctgaccaagaaccaggtcagcctgacctgcctg gtcaaaggcttctatcccagcgacatcgccgtggagtgggagagcaatgg gcagccggagaacaactacaagaccacgcctcccgtgttggactccgacg gctccttcttcctctacagcaagctcaccgtggacaagagcaggtggcag caggggaacgtcttctcatgctccgtgatgcatgaggctctgcacaacca ctacacgcagaagagcctctccctgtctccgggtaaatga In SEQ ID NO:1 shown above, the signal sequence is underlined and coding sequence for the GS15 linker sequence is shown in bold. The 5' primer sequence for FSH alpha was: ggctagcctgcaggccaccatggattactacagaaaatatgc (SEQ ID NO:5). The 3' primer sequence for FSH alpha was: tccaccgatccgcctccaccagatttgtgataataacaagtact (SEQ ID NO:6).

SEQ ID NO: 2
<u>MDYYRKYAAIFLVTLSVFLHVLHS</u>APDVQDCPECTLQENPFFSQPGAPIL

QCMGCCFSRAYPTPLRSKKTMLVQKNVTSESTCCVAKSYNRVTVMGGFKV

ENHTACHCSTCYYHKSGGGGSGGGGSGGGGSDKTHTCPPCPAPELLGGPS

VFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQK

SLSLSPGK

In SEQ ID NO:2 shown above, the signal sequence is underlined and the linker sequence is shown in bold. The Fc fragment is amino acid numbers 132-358.

Resulting full length nucleotide coding and amino acid sequences for FSH beta-Fc with 6H is tag are provided as SEQ ID NO:3 and SEQ ID NO:4, respectively.

SEQ ID NO: 3
cctgcaggccacc<u>atgaagacactccagttttttcttccttttctgttgct ggaaagcaatctgctgc</u>aatagctgtgagctgaccaacatcaccattgca atagagaaagaagaatgtcgtttctgcataagcatcaacaccacttggtg tgctggctactgctacaccagggatctggtgtataaggacccagccaggc ccaaaatccagaaaacatgtaccttcaaggaactggtatacgaaacagtg agagtgcccggctgtgctcaccatgcagattccttgtatacatacccagt ggccacccagtgtcactgtggcaagtgtgacagcgacagcactgattgta ctgtgcgaggcctggggcccagctactgctccttttggtgaaatgaaagaa ggtggaggcggatccggtggaggcgggtccggcggtggagggagcgacaa aactcacacgtgcccgccgtgcccagctccggaactgctgggcggaccgt cagtcttcctcttccccccaaaacccaaggacaccctcatgatctcccgg acccctgaggtcacatgcgtggtggtggacgtgagccacgaagaccctga ggtcaagttcaactggtacgtggacggcgtggaggtgcataatgccaaga caaagccgcgggaggagcagtacaacagcacgtaccgtgtggtcagcgtc ctcaccgtcctgcaccaggactggctgaatggcaaggagtacaagtgcaa ggtctccaacaaagccctcccagcccccatcgagaaaaccatctccaaag ccaaagggcagccccgagaaccacaggtgtacaccctgcccccatcccgg gatgagctgaccaagaaccaggtcagcctgacctgcctggtcaaaggctt ctatcccagcgacatcgccgtggagtgggagagcaatgggcagccggaga -continued
acaactacaagaccacgcctcccgtgttggactccgacggctccttcttc ctctacagcaagctcaccgtggacaagagcaggtggcagcagggggaacgt cttctcatgctccgtgatgcatgaggctctgcacaaccactacacgcaga agagcctctccctgtctccgggtaaacatcatcaccatcaccactga In SEQ ID NO:3 shown above, the signal sequence is underlined, the 6His tag is shown in italics, and the GS15 linker sequence is shown in bold. The 5' primer sequence for FSH beta was: ggctagcctgcaggccaccatgaagacactccagttttct (SEQ ID NO:7). The 3' primer sequence for FSH beta was: tccaccggatccgcctccaccttctttcatttcaccaaagga (SEQ ID NO:8).

SEQ ID NO: 4
<u>MKTLQFFFLFCCWKAICCNS</u>CELTNITIAIEKEECRFCISINTTWCAGYC

YTRDLVYKDPARPKIQKTCTFKELVYETVRVPGCAHHADSLYTYPVATQC

HCGKCDSDSTDCTVRGLGPSYCSFGEMKEGGGGSGGGGSGGGGSDKTHTC

PPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNK

ALPAPIEKTISKAKGQPREPQVYTLPPSRDELTKNQVSLTCLVKGFYPSD

IAVEWESNGQPENNYKTTPPVLDSDGSFFLYSKLTVDKSRWQQGNVFSCS

VMHEALHNHYTQKSLSLSPGK*HHHHHH*

In SEQ ID NO:4 shown above, the signal sequence is underlined, the His tag is shown in italics, and the GS15 linker sequence is shown in bold. The Fc fragment is amino acid numbers 145-371.

Example 2

Expression and Purification of Single-Chain FSH-Fc and Heterodimer FSH-Fc

Figure 2:
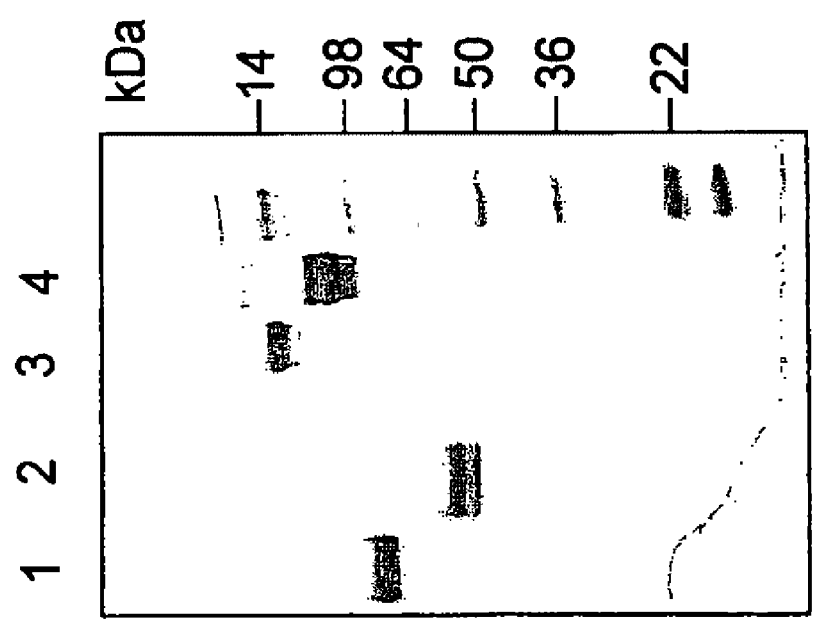
FIG. 2 is an image of an SDS-PAGE gel of single-chain FSH-Fc and heterodimer FSH-Fc run under reducing and non-reducing conditions. Lane 1, single-chain FSH-Fc reduced; lane 2, heterodimer FSH-Fc reduced; lane 3, single-chain FSH-Fc non-reduced; and lane 4, heterodimer FSH-Fc non-reduced.

Single-chain FSH-Fc was transfected into CHO DG44 cells lacking a dihydrofolate reductase gene using standard Superfect transfection protocols (Qiagen, Valencia, Calif.). After 48 h, transfected cells were selected in MEMα without ribonucleosides and deoxyribonucleosides containing 5% dialyzed FBS. To obtain higher protein expression levels, cells were treated with methotrexate at levels up to 200 nM. For expression studies, cells were seeded into roller bottles in DMEM:F12+10% FBS and incubated for three days before changing the medium to DMEM:F12+5 μg/ml human insulin. Conditioned medium was collected daily for 10 days and then filtered through 0.2 μm filters and stored at 4° C. until purification. Single-chain FSH-Fc was purified from cell supernatant using standard protein A affinity chromatography. Once medium containing single-chain FSH-Fc was loaded, protein A columns were washed with 5-10 column volumes of PBS (10 mM phosphate pH 7.4, 2.7 mM KCl and 137 mM NaCl) and bound protein eluted with 0.1 M glycine pH 3.0. Eluted single-chain FSH-Fc was then dialyzed into PBS and stored at −80° C. in aliquots containing 10% glycerol. Single-chain FSH-Fc is approximately 90% pure following a single protein A chromatography step (FIG. 2).

Heterodimer FSH-Fc was expressed by co-transfecting FSH alpha-Fc and FSH beta-Fc-6His expression vectors into CHO DG44 cells using standard Superfect transfection methods. Forty-eight hours after transfection, cells were selected in MEMα without ribonucleosides and deoxyribonucleosides containing 5% dialyzed FBS and 10 μg/ml blasticidin to select only for cells containing both FSH alpha-Fc and FSH beta-Fc expression vectors. To obtain higher expression levels, cells were treated with methotrexate up to 50 nM. For expression studies, cells were seeded into roller bottles and cell supernatant containing secreted protein collected in the same way as for single-chain FSH-Fc. Since FSH alpha-Fc and FSH beta-Fc were co-transfected, cell supernatants contained mixtures of FSH alpha-Fc homodimer, FSH beta-Fc homodimer, and heterodimer FSH-Fc that required separation. An initial purification using protein A affinity chromatography was performed in the same way as described above for single-chain FSH-Fc. After protein A elution, protein was further purified by nickel affinity chromatography. FSH beta-Fc homodimers and heterodimer FSH-Fc bind to nickel affinity columns due to the presence of a 6His, tag. Heterodimer FSH-Fc was separated from the FSH beta-Fc homodimer by elution with an imidazole gradient (0-500 mM) with the heterodimer FSH-Fc eluting at approximately 30 to 90 mM imidazole. Heterodimer FSH-Fc was approximately 90% pure following protein A and nickel affinity chromatography steps (FIG. 2).

FIG. 1c shows a schematic diagram of single-chain FSH-Fc and heterodimer FSH-Fc fusion proteins. In this example single-chain FSH-Fc is a fusion molecule of FSH alpha, FSH beta, and the Fc portion of a human IgG, molecule including the hinge, CH2, and CH3 domains. Thus an Fc dimer of single-chain FSH-Fc contained two FSH alpha and two FSH beta subunits. In contrast, in this example heterodimer FSH-Fc was made in such a way that the Fc dimer contained a single FSH alpha subunit on one Fc chain and a single FSH beta subunit on the other Fc chain. Because of the extra FSH subunits in the single-chain FSH-Fc molecule, single-chain FSH-Fc protein is larger than the heterodimer FSH-Fc protein when run under either reducing conditions (approximately 75 kDa compared to 50 kDa, respectively) or non-reducing conditions (approximately 150 kDa compared to 100 kDa, respectively) on SDS-PAGE gels (FIG. 2). Under non-reducing conditions, both single-chain FSH-Fc and heterodimer FSH-Fc predominantly form Fc dimers (FIG. 1c and FIG. 2).

Example 3

Rodent Pharmacodynamic Studies: Subcutaneous Dosing

In order to determine whether single-chain FSH-Fc and heterodimer FSH-Fc fusion proteins have similar bioactivity to human recombinant FSH, 21-day-old female rats (10 rats per group) were dosed subcutaneously with a single dose of recombinant FSH (Follistim, Organon, West Orange, N.J.), single-chain FSH-Fc, or heterodimer FSH-Fc in PBS at 1 nmol/kg. Seventy-two hours after dosing, ovarian weight was measured in each rat. Steelman S L and Pohley F M (1953) *Endocrinol* 53:604-16. Statistics were analyzed using SigmaStat version 2.0 (RockWare, Inc., Golden, Colo.). Results are presented in FIG. 3.

Figure 3:
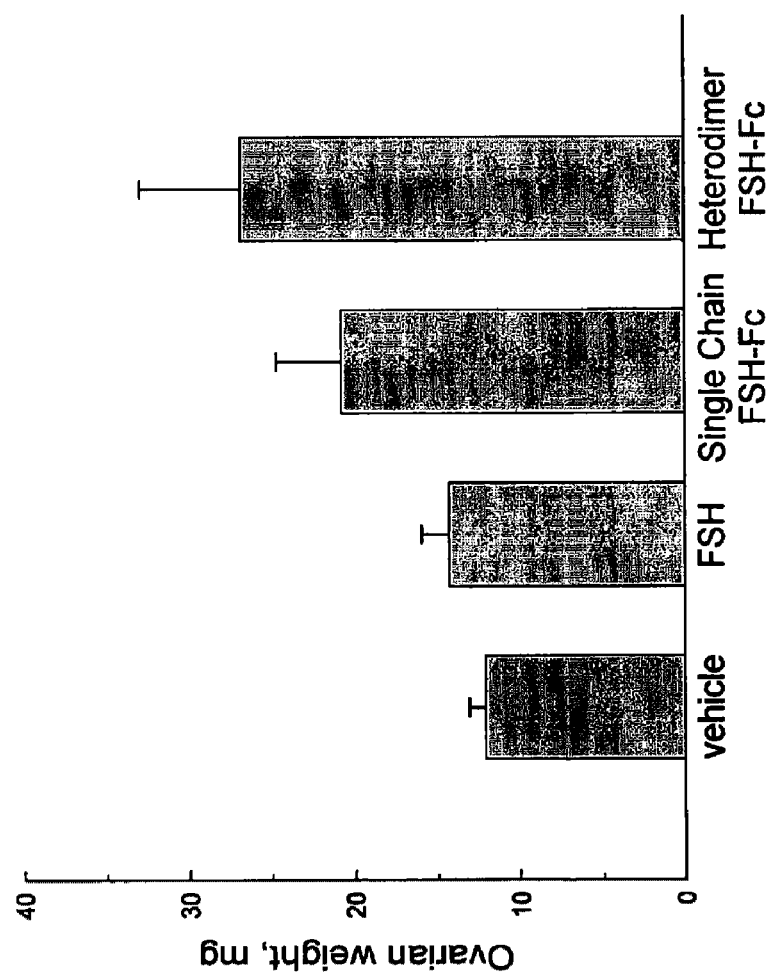
FIG. 3 is a bar graph depicting ovarian weight in 21-day-old female rats treated with a single subcutaneous dose of 1 nmol/kg recombinant FSH, single-chain FSH-Fc, or heterodimer FSH-Fc. Ovarian weight was measured 72 h after dosing. Data are presented as average ovarian weight±standard deviation (SD). n=10/group.

As shown in FIG. 3, ovarian weight was significantly increased in female rats treated with a single dose of recombinant FSH compared to vehicle (14.3±1.7 mg compared to 12.1±1.0 mg, respectively, p=0.003). However, single-chain FSH-Fc and heterodimer FSH-Fc produced an even greater increase in ovarian weight compared to vehicle and FSH treated groups (20.8±3.9 mg and 26.9±6.1 mg, respectively; p<0.001). Heterodimer FSH-Fc was significantly more active than single-chain FSH-Fc in this experiment (p=0.016).

Example 4

Rodent Pharmacokinetic Studies

Neonatal rats express high levels of FcRn in the small intestines during the first three weeks of life. This system can therefore be used to determine oral delivery of FcRn binding molecules such as Fc fusion proteins. Ten-day-old neonatal rats (four rats per group) were dosed orally with 0.3 mg/kg single-chain FSH-Fc or heterodimer FSH-Fc in normal saline containing 5 mg/ml soybean trypsin inhibitor. At various times after dosing, blood was collected by cardiac puncture and serum prepared. Serum was stored at −20° C. until analysis by ELISA. A sandwich ELISA was developed using an anti-FSH coating antibody (Fitzgerald Industries, Concord, Mass.) and a horseradish peroxidase conjugated anti-Fc detection antibody (Pierce Chemical Company, Rockford, Ill.). The standard curve for the ELISA was created with the same lot of protein used to dose the rats. Samples were analyzed in triplicate. Pharmacokinetic parameters were estimated using WinNonlin version 4.1 (Pharsight, Mountain View, Calif.). Results are presented in FIG. 4.

Figure 4:
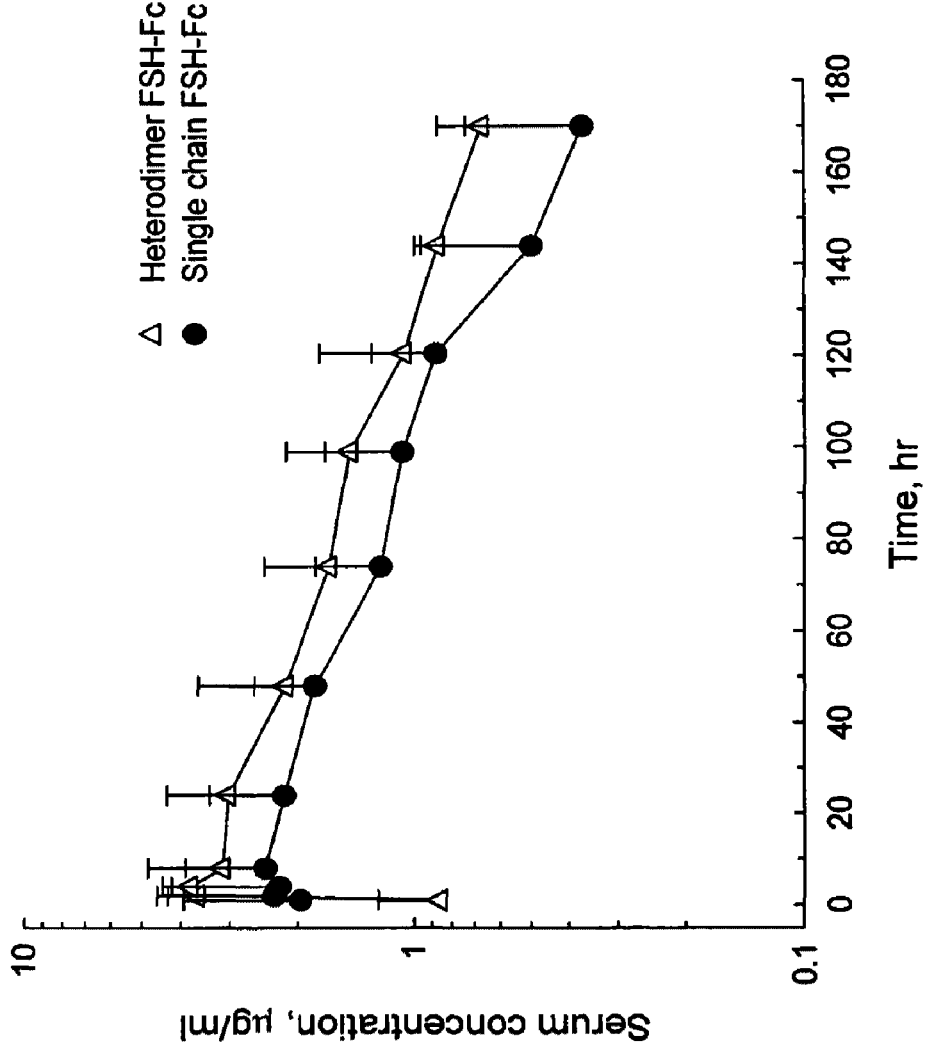
FIG. 4 is a graph depicting levels of single-chain FSH-Fc (circles) and heterodimer FSH-Fc (triangles) in neonatal rat serum after a single oral dose of 0.3 mg/kg. n=4/timepoint.

As shown in FIG. 4, high levels of single-chain FSH-Fc and heterodimer FSH-Fc were measured in neonatal rat serum after oral dosing (2.4 µg/ml and 3.8 µg/ml, respectively, which are the average maximum serum concentrations), and both proteins had long terminal half-lives of 60 h and 69 h, respectively. In combination with the bioactivity results in FIG. 3, these data suggest that the higher in vivo activity of single-chain and heterodimer FSH-Fc compared to recombinant FSH may be due to the long half-lives of the fusion proteins.

Example 5

Role of FcRn in Oral Delivery of Single-Chain FSH-Fc and Heterodimer FSH-Fc in Neonatal Rats In order to show that oral delivery of single-chain FSH-Fc and heterodimer FSH-Fc is due to FcRn binding and transcytosis, 10-day-old neonatal rats were orally dosed with a mixture of $^{125}$I-labeled single-chain FSH-Fc or heterodimer FSH-Fc and a 300-fold excess of unlabeled human IgG$_1$ (ICN, Irvine, Calif.) in normal saline with 5 mg/ml soybean trypsin inhibitor. Single-chain FSH-Fc and heterodimer FSH-Fc were iodinated with $^{125}$I sodium iodide (Perkin Elmer, Boston, Mass.) using iodobeads (Pierce) according to manufacturers' protocols. Free iodine was separated from iodinated protein on a PD-10 desalting column. Two hours after dosing, blood was collected by cardiac puncture and serum prepared. A 100 µl aliquot of serum was incubated with protein A tris acrylamide beads (Pierce) at 4° C. for 1 h. Protein A beads were then washed twice with PBS and eluted with SDS sample buffer containing 10% β-mercaptoethanol. Samples were boiled and analyzed on 4-20% SDS-PAGE gels, dried, and quantitation was performed on a Storm Phosphorimager (Molecular Dynamics, Piscataway, N.J.). Results are presented in FIG. 5.

Oral delivery of both single-chain FSH-Fc and heterodimer FSH-Fc was greatly reduced in the presence of excess IgG$_1$ (83% and 53% reduction in transport respectively as determined by phosphorimage analysis). Since IgG$_1$ is a natural ligand for FcRn, this suggests that single-chain FSH-Fc and heterodimer FSH-Fc bind specifically to, and are transported by, FcRn, and the process can be disrupted by the presence of excess IgG$_1$.

Example 6

Rodent Pharmacodynamic Studies: Oral Dosing

Two-day-old male rats (10 rats per group) were orally dosed with 1 nmol/kg recombinant human FSH (Follistim, Organon), single-chain FSH-Fc, or heterodimer FSH-Fc in PBS with 5 mg/ml soybean trypsin inhibitor. Rats were dosed daily for 14 days before the right testis from each animal was removed and weighed. Meachem S J et al. (1996) *Biol Reprod* 54:36-44. Statistics were analyzed using SigmaStat version 2.0 (RockWare, Inc.). Results are presented in FIG. 6.

Figure 6A:
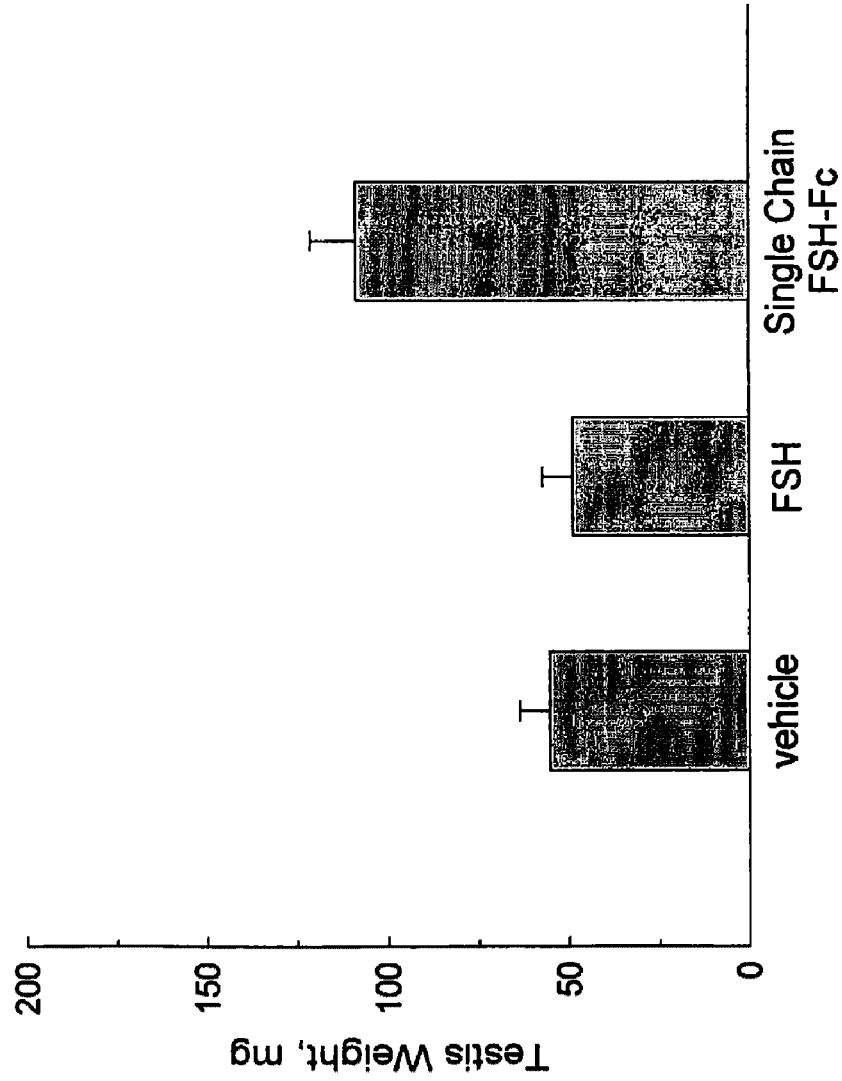
FIG. 6 is a pair of bar graphs depicting testis weight in two-day-old male rats treated daily for 14 days with single oral doses (1 nmol/kg) of (a) recombinant FSH or single-chain FSH-Fc, and (b) single-chain FSH-Fc or heterodimer FSH-Fc. Data presented as average testis weight±SD. n=6-10/group.
Figure 6B:
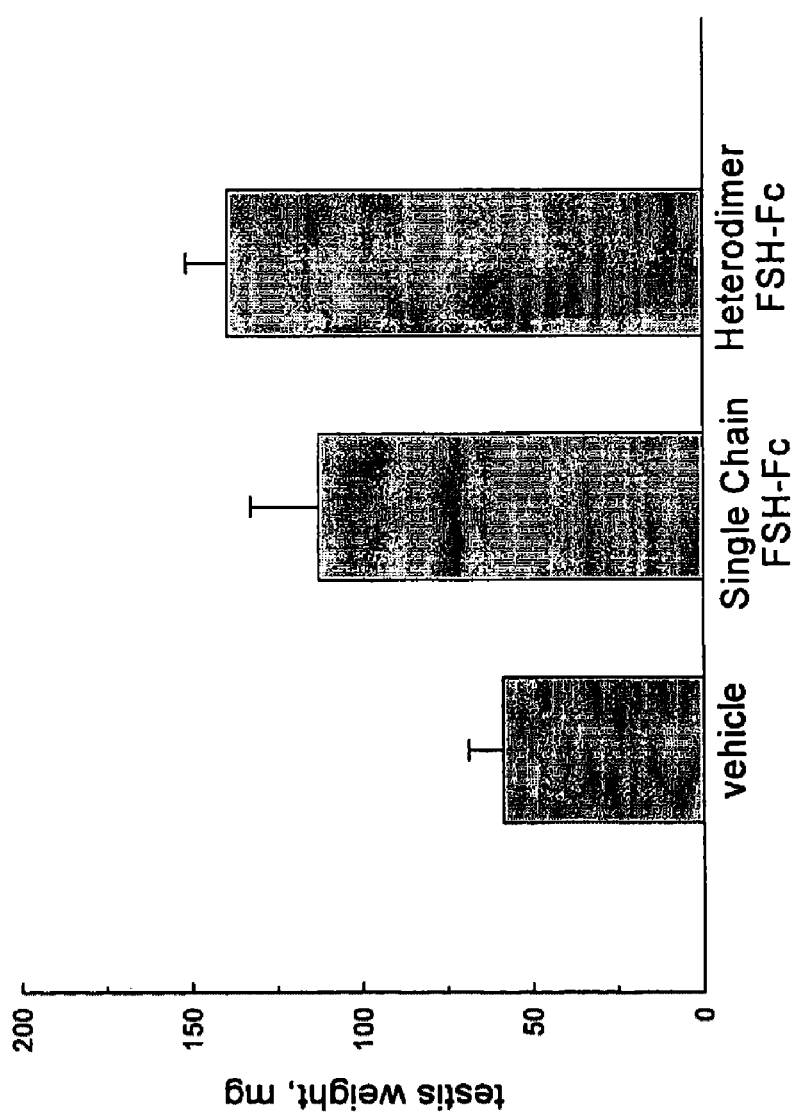

As shown in FIG. 6, in this assay recombinant FSH did not produce an increase in testis weight compared to the vehicle treated group (49.1±8.1 mg compared to 55.4±8.1 mg, respectively), suggesting that recombinant FSH was not orally active in this model (FIG. 6a). In contrast, single-chain FSH-Fc (FIG. 6a and FIG. 6b) and heterodimer FSH-Fc (FIG. 6b) treatments resulted in significant increases in testis weight compared to vehicle treated animals (113.0±19.8 mg and 139.6±11.9 mg compared to 58.6±10.4 mg, respectively; p<0.001). Similarly to the subcutaneous dosing experiment, heterodimer FSH-Fc was significantly more active than single-chain FSH-Fc in this experiment (p=0.003).

Example 7

Pharmacokinetic Studies in Cynomolgus Monkeys

We have previously shown expression of FcRn in cynomolgus monkey and human lung, and that an erythropoietin-Fc fusion protein is absorbed and retains activity after pulmonary administration (Spiekermann G M et al. (2002) *J Exp Med* 196: 300-310; Bitonti A J et al. (2004) *Proc Natl Acad Sci USA* 101: 9763-9768). We therefore next wanted to determine whether single-chain FSH-Fc and heterodimer FSH-Fc could be dosed through the lung in a non-human primate and retain biological activity.

Figure 7A:
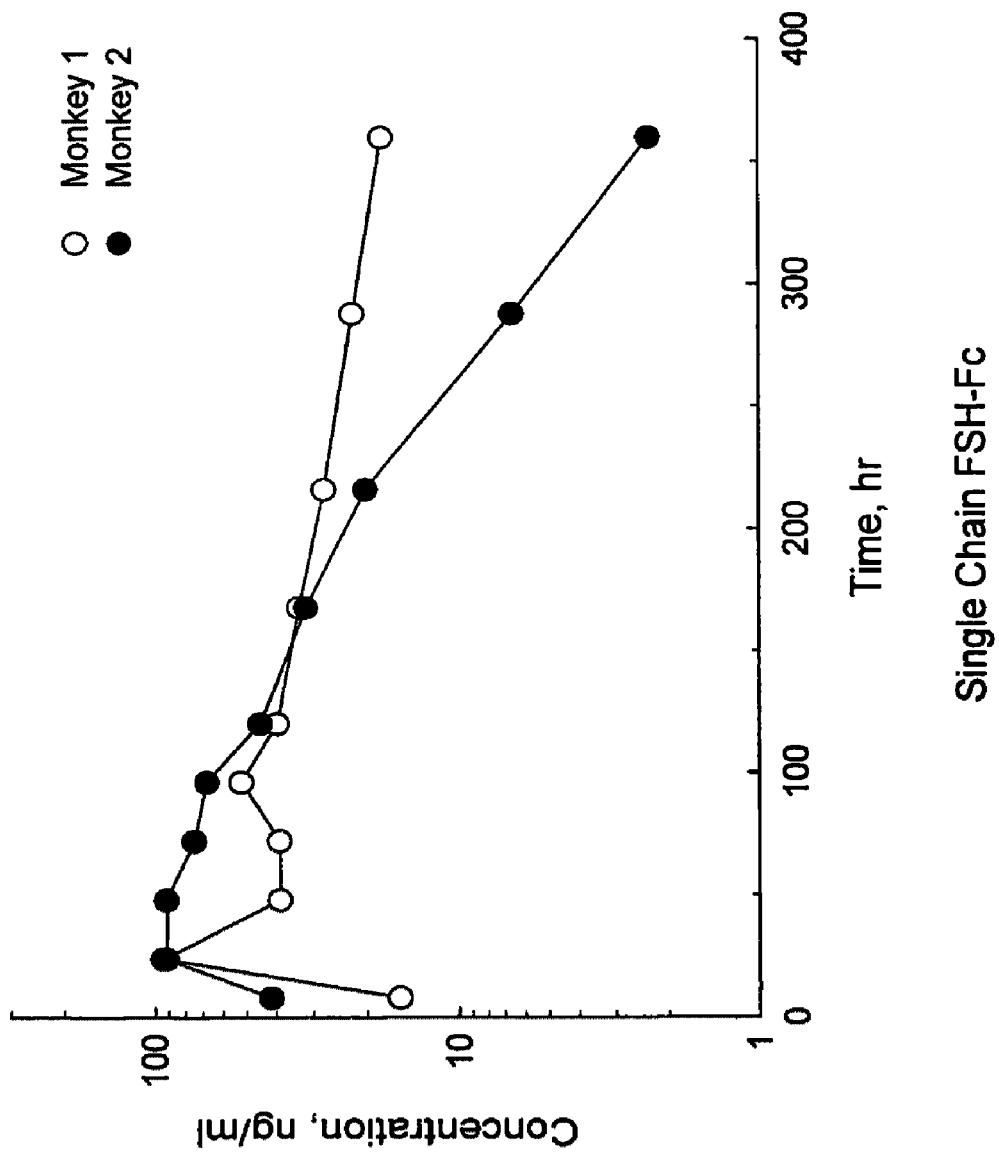
FIG. 7 is a pair of graphs depicting concentration-time profiles of (a) single-chain FSH-Fc and (b) heterodimer FSH-Fc in cynomolgus monkey serum following a single deposited pulmonary dose of 45 µg/kg. Each curve is representative of a single monkey.
Figure 7B:
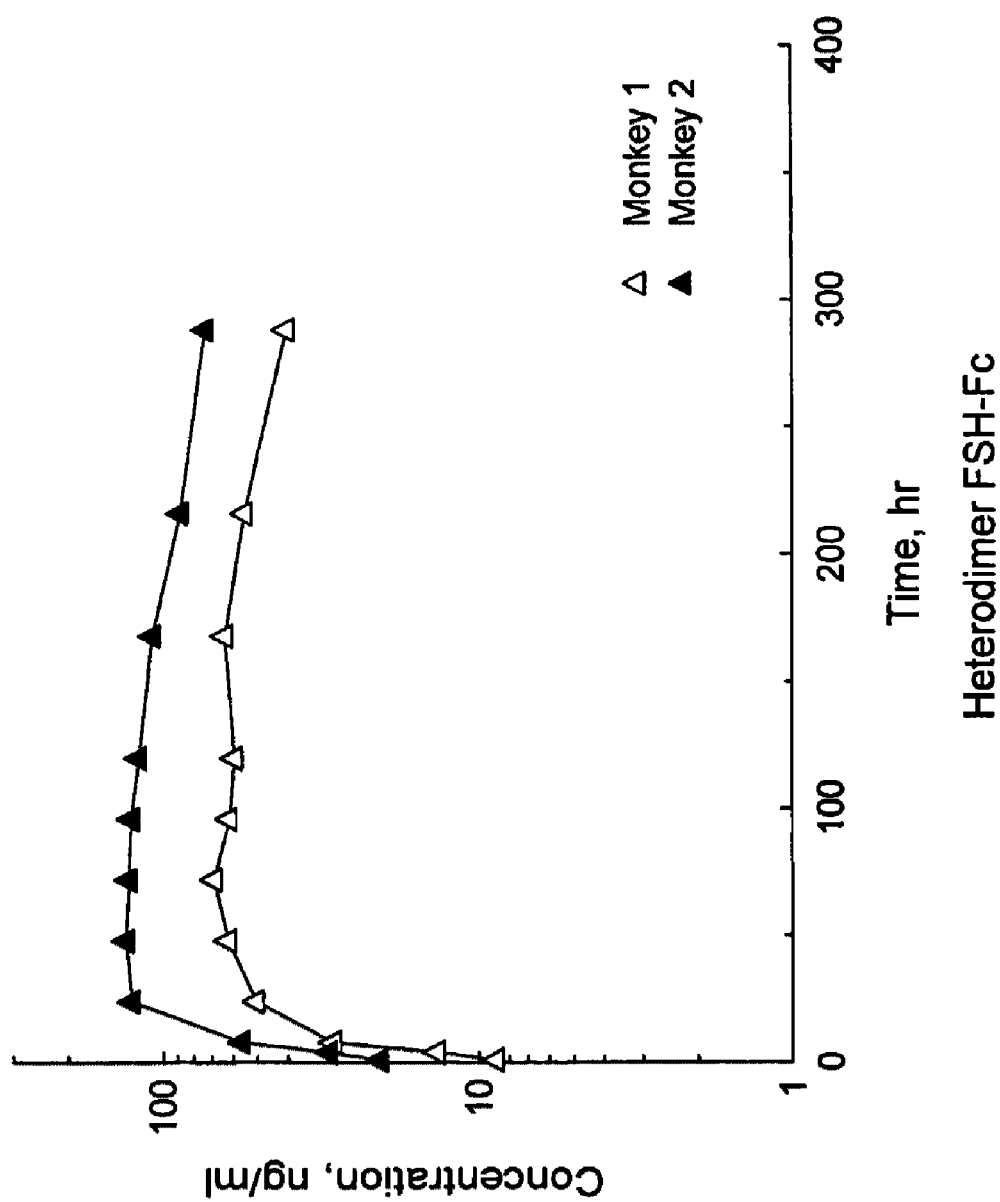

All studies with cynomolgus monkeys were conducted using approved protocols, following NIH guidelines for the care and use of research animals. Prior to pulmonary administration, animals were anesthetized with a combination of ketamine and Valium and intubated with endotracheal tubes. Aerosols of single-chain FSH-Fc (in PBS pH7.4) and heterodimer FSH-Fc (in PBS pH7.4 with 0.1% human serum albumin) were created with an Aeroneb Pro™ nebulizer (Aerogen, Mountain View, Calif.) and administered to cynomolgus monkeys (deposited dose approximately 45 µg/kg) through the endotracheal tubes. A Bird Mark 7A respirator regulated the depth (20-40% vital capacity) and rate (28-30 breaths per minute) of respiration of each monkey such that the delivery of single-chain FSH-Fc and heterodimer FSH-Fc was targeted to the central airways. Aerosol particle size was approximately 4-5 µm. Blood samples were collected at various times after pulmonary dosing and serum prepared. Serum single-chain FSH-Fc and heterodimer FSH-Fc levels were quantified using a commercially available FSH ELISA kit (DRG International, Mountainside, N.J.) according to manufacturer's directions. The standard curve for each assay was created with the same lot of single-chain FSH-Fc or heterodimer FSH-Fc used to dose the monkeys. Pharmacokinetic parameters were estimated using WinNonlin version 4.1 (Pharsight). Results are presented in Table 2 and FIG. 7.

TABLE 2

Pharmacokinetic parameter estimates after pulmonary dosing of single-chain FSH-Fc and heterodimer FSH-Fc in cynomolgus monkeys at a deposited dose of approximately 45 μg/kg.

| | single-chain FSH-Fc | | heterodimer FSH-Fc | |
|---|---|---|---|---|
| Parameter | Monkey 1 | Monkey 2 | Monkey 3 | Monkey 4 |
| Cmax, ng/ml | 91.4 | 93.9 | 68.7 | 130.5 |
| $t_{1/2}$, h | 210 | 54.7 | 182 | 219 |
| AUC, hr * ng/ml | 17489 | 13086 | 26526 | 53001 |

Deposited doses of approximately 45 μg/kg of each protein resulted in maximum serum concentrations of 91 and 94 ng/ml single-chain FSH-Fc and 69 and 131 ng/ml heterodimer FSH-Fc (Table 2). The terminal half-life of both proteins was measured as 55 and 210 h for single-chain FSH-Fc and 182 and 219 h for heterodimer FSH-Fc (Table 2). These half-lives are significantly longer than that of recombinant FSH, which is approximately 24 h in humans (Ie Cotonnec J-Y et al. (1994) *Fertil Steril* 61:679-686 and in non-human primates (Porchet H C et al. (1993) *Drug Metab Dispos* 21:144-150; Weinbauer G F et al. (1994) *J Endocrinol* 141:112-121). Thus an advantage of using FSH-Fc fusion) proteins in treatment of infertility would be the potential for greatly reduced dosing frequency.

Example 8

Pharmacodynamic Measurements in Cynomolgus Monkeys

Figure 8A:
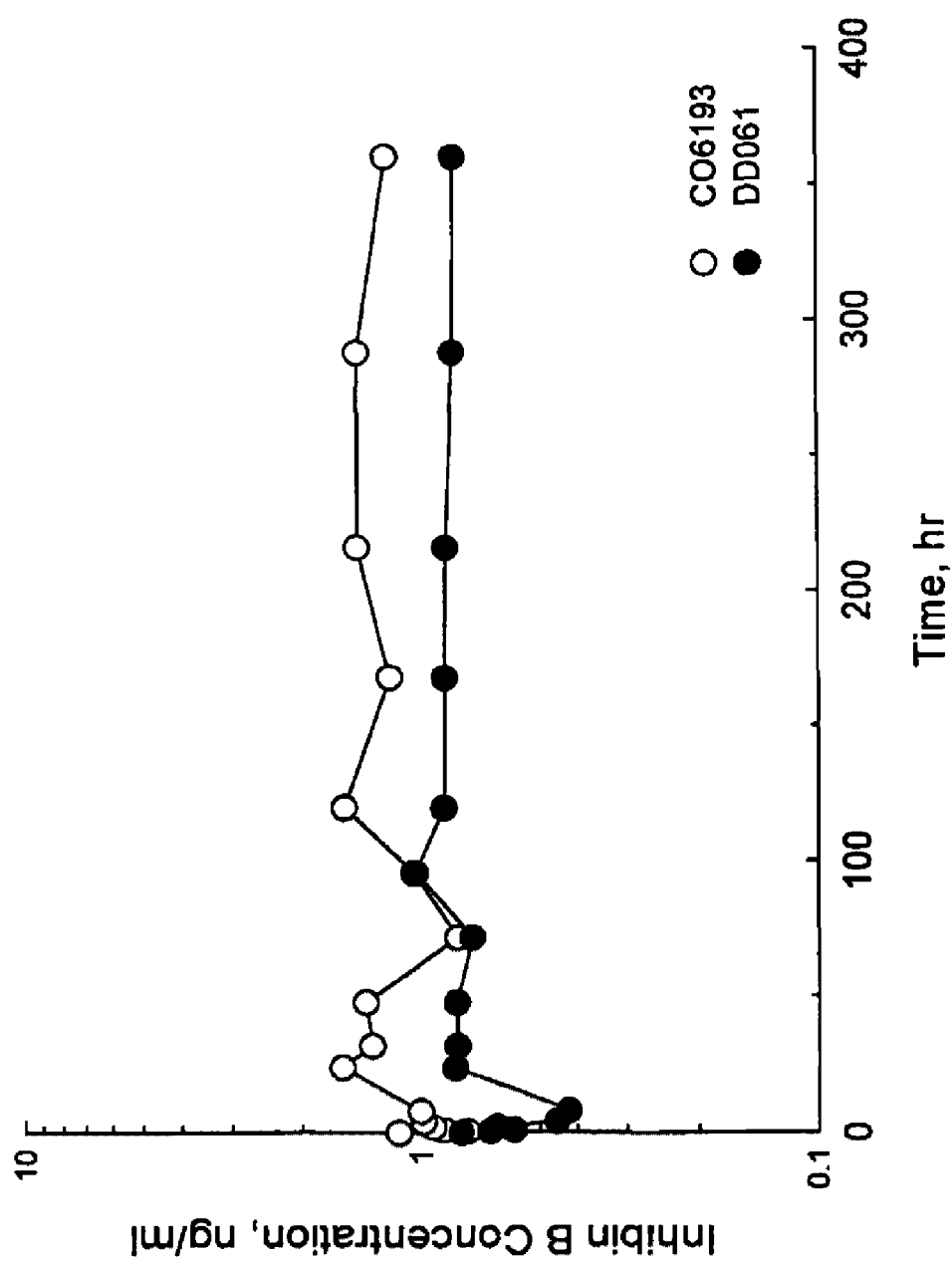
FIG. 8 is a pair of graphs depicting inhibin B concentration-time profiles in cynomolgus monkey serum following a single deposited pulmonary dose of 45 µg/kg of (a) single-chain FSH-Fc and (b) heterodimer FSH-Fc. Each curve is representative of a single monkey.
Figure 8B:
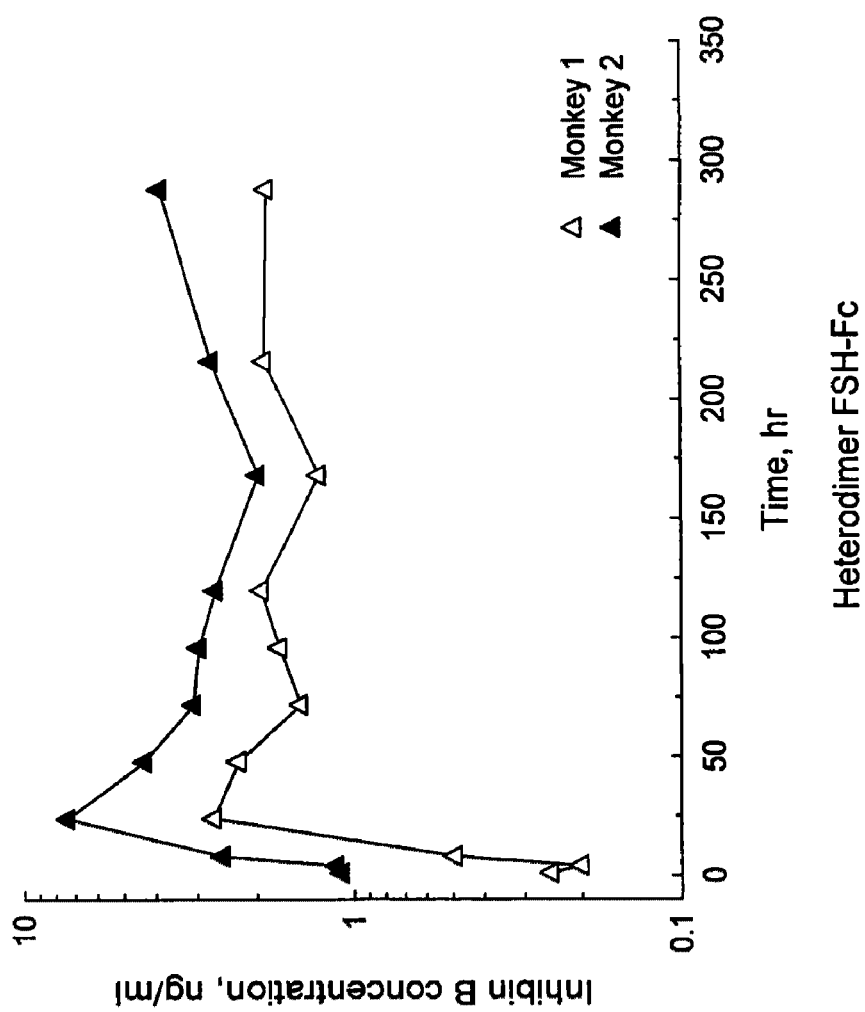

Inhibin is a pharmacodynamic marker of FSH activity. Therefore serum samples obtained after pulmonary dosing of single-chain FSH-Fc and heterodimer FSH-Fc were also used to determine inhibin levels using a commercially available ELISA kit (Diagnostic Systems Laboratories, Webster, Tex.) following manufacturer's instructions. Weinbauer G F et al. (1994) *J Endocrinol* 141:113-121. Results are presented in FIG. 8. Deposited pulmonary doses of approximately 45 μg/kg single-chain FSH-Fc resulted in maximum inhibin B concentrations of 1 and 1.6 ng/ml, equivalent to 1.2- and 1.4-fold stimulation above baseline levels. The same deposited pulmonary dose of heterodimer FSH-Fc resulted in maximum inhibin B concentrations of 2.7 and 7.4 ng/ml, equivalent to 7.1- and 5.9-fold stimulation above baseline. Fourteen days after treatment with pulmonary heterodimer FSH-Fc, inhibin B levels had not returned to baseline.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being so modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

I claim:

1. A method for increasing FSH activity in a subject in need thereof, the method comprising administering to the subject an effective amount of a heterodimeric fusion protein comprising two associated polypeptide chains, the first chain comprising an alpha subunit of follicle stimulating hormone (α-FSH) conjugated to an FcRn binding partner and the second chain comprising a beta subunit of follicle stimulating hormone (β-FSH) conjugated to an FcRn binding partner, wherein said heterodimeric fusion protein increases FSH activity in said subject.

2. The method of claim 1, wherein the subject is a human.

3. The method of claim 2, wherein the human is a female.

4. The method of claim 3, wherein the increased FSH activity improves fertility in said female.

5. The method of claim 3, wherein said female is infertile and is undergoing in vitro fertilization.

6. The method of claim 2, wherein the human is a male.

7. The method of claim 2, wherein the heterodimeric fusion protein increases gonadal weight in said human.

8. The method of claim 1, wherein the fusion protein is administered intravenously, intramuscularly, subcutaneously, orally, buccally, sublingually, nasally, rectally, vaginally, via an aerosol, or via a pulmonary route.

9. The method of claim 1, wherein said first chain or second chain further comprises a linker between the FSH subunit and the FcRn binding partner.

10. The method of claim 9, wherein said linker comprises 15 amino acids.

11. The method of claim 9, wherein said linker is selected from the group consisting of (GGS)n and (GGGGS)n, wherein n is 1, 2, 3, 4, 5, 6, 7, 8, 9, or 10.

12. The method of claim 9, wherein said linker is selected from the group consisting of GGG, SEQ ID NO: 16, SEQ ID NO: 17, SEQ ID NO: 18, SEQ ID NO: 10, and SEQ ID NO: 9.

13. The method of claim 9, wherein said linker is a non-peptide linker.

14. The method of claim 1, wherein said FcRn binding partner is an Fc fragment.

15. The method of claim 14, wherein said Fc fragment is amino acids 145 to 371 of SEQ ID NO: 4.

16. The method of claim 1, wherein said first chain comprises SEQ ID NO: 2 and said second chain comprises SEQ ID NO: 4.

17. The method of claim 1, wherein said first chain is encoded by SEQ ID NO: 1 and said second chain is encoded by SEQ ID NO: 3.

18. The method of claim 1, wherein said fusion protein has the formula:

αFSH-L-Fc:βFSH-L-Fc wherein αFSH is an alpha subunit of FSH, βFSH is a beta subunit of FSH, L is a linker or direct bond, Fc is an Fc fragment of an immunoglobulin, the colon (:) is an association between the polypeptide chains, wherein the carboxy termini of αFSH and βFSH are linked directly or indirectly through L to the amino terminus of the respective Fc.

19. The method of claim 1, wherein said fusion protein has the formula:

Fc-L-αFSH:Fc-L-βFSH wherein αFSH is an alpha subunit of FSH, βFSH is a beta subunit of FSH, L is a linker or direct bond, Fc is an Fc fragment of an immunoglobulin, the colon (:) is an association between the polypeptide chains, wherein the amino termini of αFSH and βFSH are linked directly or indirectly through L to the carboxy terminus of the respective Fc.

* * * * *